(12) United States Patent
Shelton, IV et al.

(10) Patent No.: US 10,555,734 B2
(45) Date of Patent: Feb. 11, 2020

(54) METHODS AND SYSTEMS FOR MATING CONSTRICTABLE ADJUNCT MATERIALS WITH END EFFECTORS

(71) Applicant: Ethicon LLC, Guaynabo, PR (US)

(72) Inventors: Frederick E. Shelton, IV, Hillsboro, OH (US); Prudence Vulhop, Cincinnati, OH (US); Jason L. Harris, Lebanon, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 435 days.

(21) Appl. No.: 15/435,891

(22) Filed: Feb. 17, 2017

(65) Prior Publication Data

US 2018/0235620 A1 Aug. 23, 2018

(51) Int. Cl.
*A61B 17/072* (2006.01)
*A61B 17/115* (2006.01)
*A61B 17/00* (2006.01)

(52) U.S. Cl.
CPC .... *A61B 17/07207* (2013.01); *A61B 17/1155* (2013.01); *A61B 2017/00473* (2013.01);
(Continued)

(58) Field of Classification Search
CPC ........ A61B 17/07207; A61B 17/07292; A61B 17/1155; A61B 2017/07257;
(Continued)

(56) References Cited

U.S. PATENT DOCUMENTS 7,143,925 B2 12/2006 Shelton, IV et al.
7,601,118 B2 10/2009 Smith et al.
(Continued)

FOREIGN PATENT DOCUMENTS

EP 3072458 A2 9/2016
WO WO-2008057281 A2 5/2008

OTHER PUBLICATIONS

Extended European Search Report for EP App. No. 18157194.4 dated May 4, 2018 (7 pages).
(Continued)

*Primary Examiner* — Robert F Long
(74) *Attorney, Agent, or Firm* — Mintz Levin Cohn Ferris Glovsky and Popeo, P.C.

(57) ABSTRACT

Systems and methods for releasably coupling an adjunct material to an end effector for a surgical instrument are provided. The adjunct can be configured to be releasably retained on a jaw, such as a cartridge or anvil, using a contractible attachment feature configured to be transitioned from an original, non-contracted configuration to a contracted configuration under application of heat. The attachment feature, such as one or more strands of a shrinkable polymer, can be engaged with the adjunct, and contraction of the attachment feature is effective to couple the adjunct with retaining members formed on the jaw. Another type of an adjunct has at least one portion configured to be reversibly stretched using application of a force such that, when the force is removed, the portion transitions from a stretched configuration to a contracted configuration and thereby causes the adjunct to be engaged with retaining members formed on the jaw.

10 Claims, 16 Drawing Sheets

(52) U.S. Cl.
CPC .............. *A61B 2017/00526* (2013.01); *A61B 2017/07271* (2013.01)

(58) Field of Classification Search
CPC .......... A61B 2017/07271; A61B 2017/00473; A61B 2017/00871; A61B 2017/00526; A61B 2017/0046
USPC .......................................... 227/175.1–182.1
See application file for complete search history.

(56) References Cited

U.S. PATENT DOCUMENTS

| | | | |
|---|---|---|---|
| 8,317,070 B2 | 11/2012 | Hueil et al. | |
| 8,393,514 B2 | 3/2013 | Shelton, IV et al. | |
| 9,282,962 B2 | 3/2016 | Schmid et al. | |
| 9,757,124 B2* | 9/2017 | Schellin | B29C 55/00 |
| 9,839,422 B2* | 12/2017 | Schellin | B29C 55/00 |
| 9,839,423 B2* | 12/2017 | Vendely | B29C 55/00 |
| 9,848,871 B2* | 12/2017 | Harris | A61B 17/0686 |
| 9,943,310 B2* | 4/2018 | Harris | A61B 17/0644 |
| 10,265,074 B2* | 4/2019 | Shelton, IV | A61B 17/068 |
| 10,307,160 B2* | 6/2019 | Vendely | A61B 17/072 |
| 2005/0267325 A1* | 12/2005 | Bouchier | A61B 17/06004 600/37 |
| 2009/0297582 A1* | 12/2009 | Meyer | A61B 17/12022 424/423 |
| 2010/0065606 A1* | 3/2010 | Stopek | A61B 17/072 227/176.1 |
| 2011/0087279 A1* | 4/2011 | Shah | A61B 17/07207 606/219 |
| 2012/0150176 A1 | 6/2012 | Weizman | |
| 2013/0068820 A1 | 3/2013 | Miller et al. | |
| 2013/0221065 A1 | 8/2013 | Aronhalt et al. | |
| 2013/0256377 A1 | 10/2013 | Schmid et al. | |
| 2014/0158741 A1 | 6/2014 | Woodard, Jr. et al. | |
| 2014/0224686 A1* | 8/2014 | Aronhalt | A61B 17/068 206/339 |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0238185 A1* | 8/2015 | Schellin | A61B 17/07207 227/175.1 |
| 2015/0238187 A1* | 8/2015 | Schellin | A61B 17/07207 227/180.1 |
| 2015/0238188 A1* | 8/2015 | Vendely | A61B 17/07207 227/175.1 |
| 2015/0272575 A1 | 10/2015 | Leimbach et al. | |
| 2015/0277471 A1 | 10/2015 | Leimbach et al. | |
| 2015/0351754 A1* | 12/2015 | Harris | A61B 17/0686 606/219 |
| 2015/0351758 A1 | 12/2015 | Shelton, IV et al. | |
| 2015/0351763 A1* | 12/2015 | Shelton, IV | A61B 17/068 227/176.1 |
| 2016/0089142 A1 | 3/2016 | Harris et al. | |
| 2017/0055986 A1 | 3/2017 | Harris et al. | |
| 2017/0056568 A1* | 3/2017 | Shelton, IV | A61L 31/148 |
| 2017/0086832 A1* | 3/2017 | Harris | A61B 17/08 |
| 2017/0086836 A1* | 3/2017 | Harris | A61B 17/068 |
| 2017/0086838 A1* | 3/2017 | Harris | A61B 17/068 |
| 2017/0086840 A1* | 3/2017 | Harris | A61B 17/068 |
| 2017/0086842 A1* | 3/2017 | Shelton, IV | A61B 17/105 |
| 2017/0086843 A1* | 3/2017 | Vendely | A61B 17/07207 |
| 2017/0086844 A1* | 3/2017 | Vendely | A61B 17/068 |
| 2017/0086845 A1* | 3/2017 | Vendely | A61B 17/068 |
| 2018/0235591 A1* | 8/2018 | Vendely | A61B 17/29 |
| 2018/0235612 A1* | 8/2018 | Shelton, IV | A61B 17/07207 |
| 2018/0235626 A1* | 8/2018 | Shelton, IV | A61B 17/07207 |

OTHER PUBLICATIONS

U.S. Appl. No. 14/926,194 entitled "Extensible Buttress Assembly for Surgical Stapler", filed Oct. 29, 2015.
U.S. Appl. No. 15/385,953 entitled "Methods of Stapling Tissue", filed Dec. 21, 2016.
U.S. Appl. No. 15/435,986 entitled "Surgical End Effector Adjunct Attachment", filed Feb. 17, 2017.

* cited by examiner

METHODS AND SYSTEMS FOR MATING CONSTRICTABLE ADJUNCT MATERIALS WITH END EFFECTORS

FIELD

The present disclosure relates generally to adjunct materials used in conjunction with an end effector of a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

An end effector for a surgical instrument is provided that in some embodiments includes a first jaw having a cartridge with a plurality of staple cavities configured to seat staples therein, the staple cavities opening on a tissue-facing surface of the cartridge, and a second jaw opposing the first jaw and having an anvil with a plurality of staple forming cavities formed on a tissue-facing surface thereof. The first and second jaws are configured to clamp tissue therebetween. The end effector also includes at least first and second retaining members disposed on a tissue-facing surface of at least one jaw of the first and second jaws. The end effector further includes an adjunct material configured to be releasably retained on the at least one jaw, and a contractible attachment feature configured to be transitioned from an original, non-contracted configuration to a contracted configuration under application of heat. The attachment feature can be engaged with the adjunct material, and contraction of the attachment feature is effective to couple the adjunct material with the first and second retaining members.

The end effector can vary in different ways. For example, the at least one first retaining member can be disposed at one side of a tissue-facing surface of the at least one jaw in proximity to one edge of the tissue-facing surface of the at least one jaw, and the at least one second retaining member can be disposed at another, opposed side of the tissue-facing surface in proximity to another, opposed edge of the tissue-facing surface.

The attachment feature can have a variety of configurations. For example the attachment feature can be disposed over at least a portion of the adjunct material and can include a strand of a shrinkable polymer that can be arranged in at least one loop encompassing both the first and second retaining members. The shrinkable polymer can be contracted such that the at least one loop is engaged around the first and second retaining members thereby releasably retaining the adjunct material over the at least one jaw. In some embodiments, the strand of the shrinkable polymer can pass through at least one portion of the adjunct material. In some embodiments, the attachment feature can include a plurality of polymer strands interwoven into the adjunct material such that at least one first strand can be disposed along a longitudinal axis of the adjunct material and at least one second strand can be disposed along an axis substantially perpendicular to the longitudinal axis.

In some embodiments, the adjunct material can include a plurality of through openings, the openings having at least first and second openings configured to be mated with the first and second retaining members when the plurality of polymer strands are in the contracted configuration, thereby causing the at least the first and second openings in the adjunct material to constrict around the first and second retaining members. In some embodiments, the polymer strands can be interwoven into the adjunct material by being passed through at least some of the plurality of through openings.

In another aspect, a method of assembling an end effector for a surgical instrument is provided. The end effector has a first jaw having a cartridge with a plurality of staple cavities configured to seat staples therein and opening on a tissue-facing surface of the cartridge, and a second jaw opposing the first jaw and having an anvil with a plurality of staple forming cavities formed on a tissue-facing surface thereof. The method includes associating an adjunct material with at least one contractible attachment feature configured to be transitioned from an original, non-contracted configuration to a contracted configuration under application of heat, and applying heat to the adjunct material to cause the at least one contractible attachment feature to contract and thereby cause the adjunct material to be releasably retained on the at least one jaw by coupling the adjunct material with first and second retaining members disposed on a tissue facing surface of at least one jaw of the first and second jaws.

The method can vary in a number of ways. For example, applying the heat to the adjunct material to cause the at least one contractible attachment feature to contract and thereby cause the adjunct material to be releasably retained on the at least one jaw further can include coupling the at least one contractible attachment feature with first and second retaining members.

In another aspect, an end effector for a surgical instrument is provided that in some embodiments includes a first jaw having a cartridge with a plurality of staple cavities configured to seat staples therein, the staple cavities opening on a tissue-facing surface of the cartridge, and a second jaw opposing the first jaw and having an anvil with a plurality of staple forming cavities formed on a tissue-facing surface thereof. The first and second jaws are configured to clamp tissue therebetween. The end effector also includes at least one first and second retaining members disposed on a tissue-facing surface of at least one jaw of the first and second jaws. The end effector further includes an adjunct material that includes at least one first portion that is configured to be reversibly stretched using application of a force such that, when the force is removed, the first portion transitions from a stretched configuration to a contracted configuration and thereby causes the adjunct material to be engaged with the first and second retaining members.

The end effector can vary in various ways. For example, in some embodiments, the first portion of the adjunct material can configured to be reversibly stretched using a removable loader member configured to releasably retain the adjunct material thereon until the adjunct material is applied to the at least one jaw. As another example, the first and second retaining members can be received in respective first and second openings in the adjunct material.

In some embodiments, the adjunct material can include at least one second, substantially non-stretchable portion. The at least one second portion can be disposed at a suitable location of the adjunct material. For example, the at least one second portion can be disposed at an area of the adjunct configured to be penetrated by the staples as the staples are ejected from the staple cavities. In some embodiments, the at least one second portion can be part of the adjunct material, and the at least one second portion can have at least one property that is different from at least one property of other portions of the adjunct material.

In some embodiments, the at least one second portion is or includes at least one portion of a separate, substantially non-stretchable material coupled with the adjunct material. The at least one second portion can be at least one sheet laminate disposed over the adjunct material.

In some embodiments, the adjunct material is a first adjunct material, and the end effector includes a substantially non-stretchable second adjunct material that is coupled to and disposed over the first adjunct material. The second adjunct material can be configured to reinforce and/or treat a treatment site in a patient, and the first adjunct material can be configured to engage the first and second adjunct materials with the first and second retaining members.

BRIEF DESCRIPTION OF DRAWINGS

This disclosure will be more fully understood from the following detailed description taken in conjunction with the accompanying drawings, in which.

DETAILED DESCRIPTION

Figure 1:
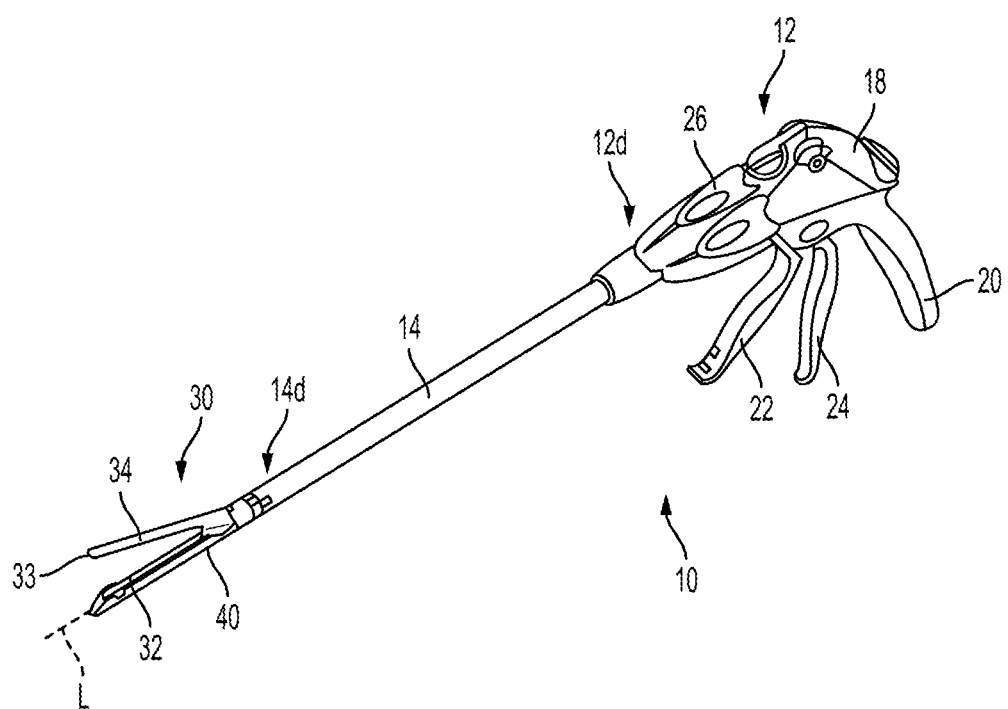
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon.

Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.).

It will be recognized by one skilled in the art that a staple puncture site may serve as a stress concentration and that the size of the hole created by the staple will grow when the tissue around it is placed under tension. Restricting the tissue movement around these puncture sites can minimize any increase in the size of the holes when subjected to tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example, linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used on a variety of tissues in a variety of different surgical procedures, for example in thoracic surgery or in gastric surgery.

Figure 2:
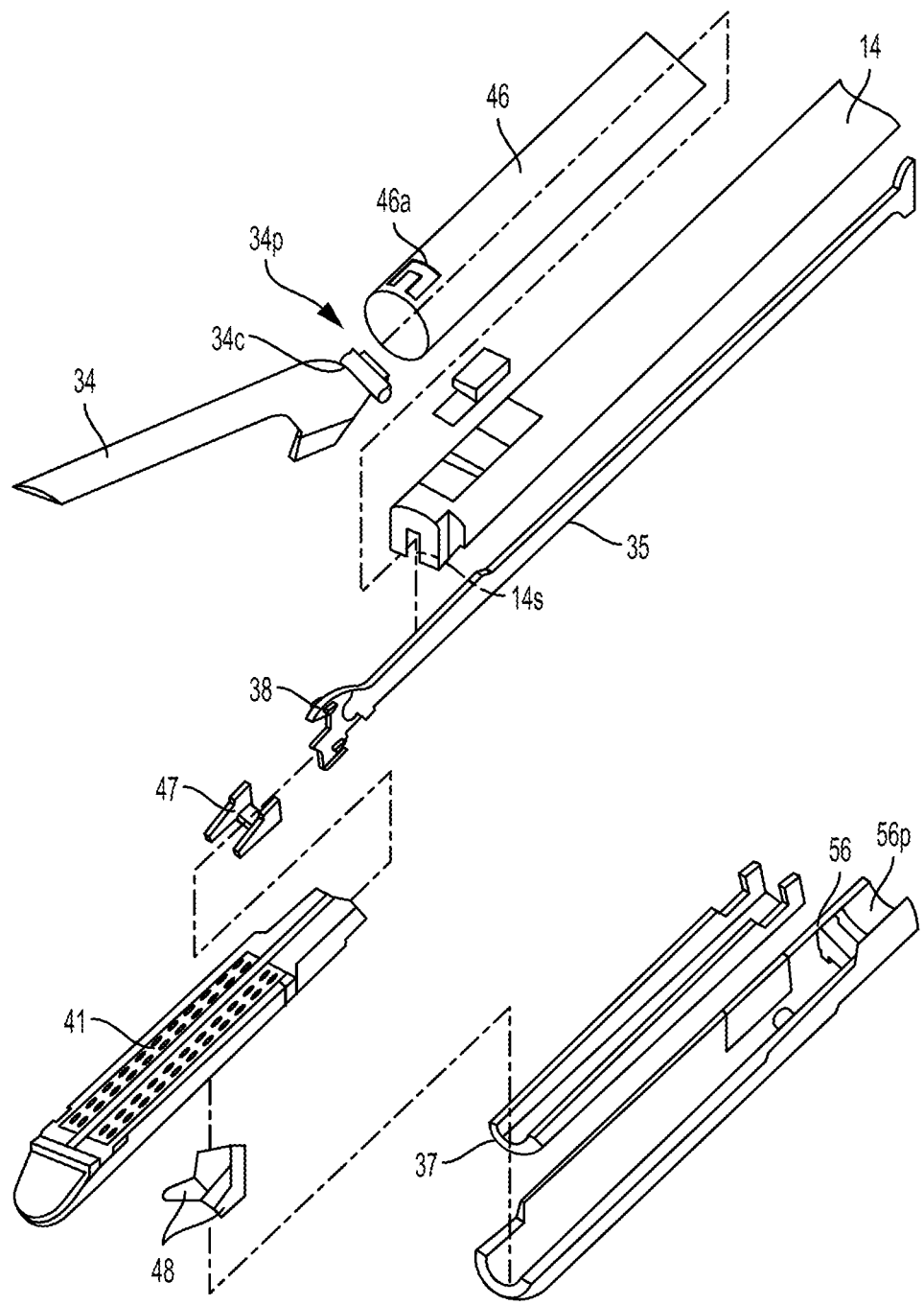
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
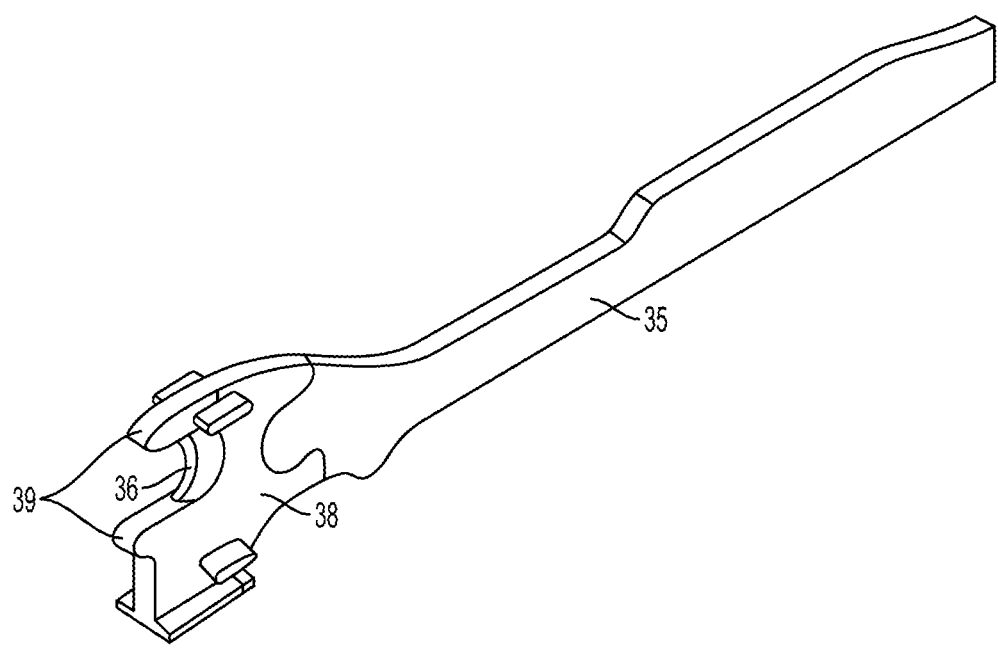
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
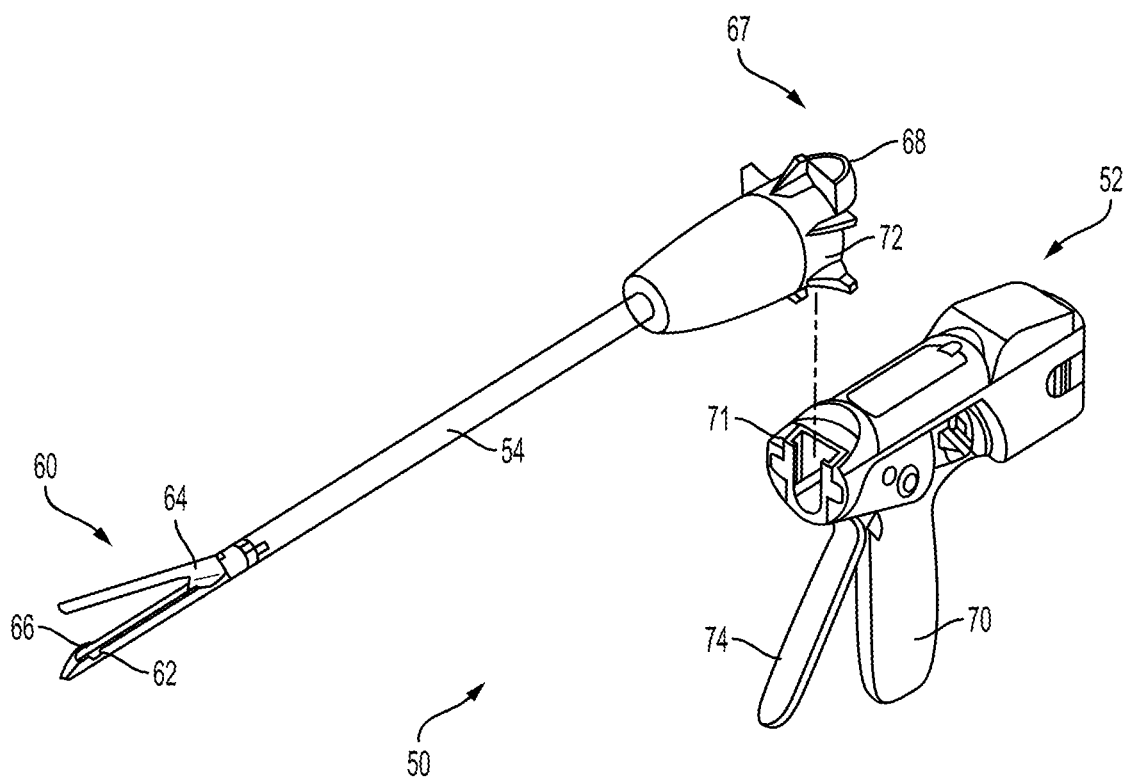
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
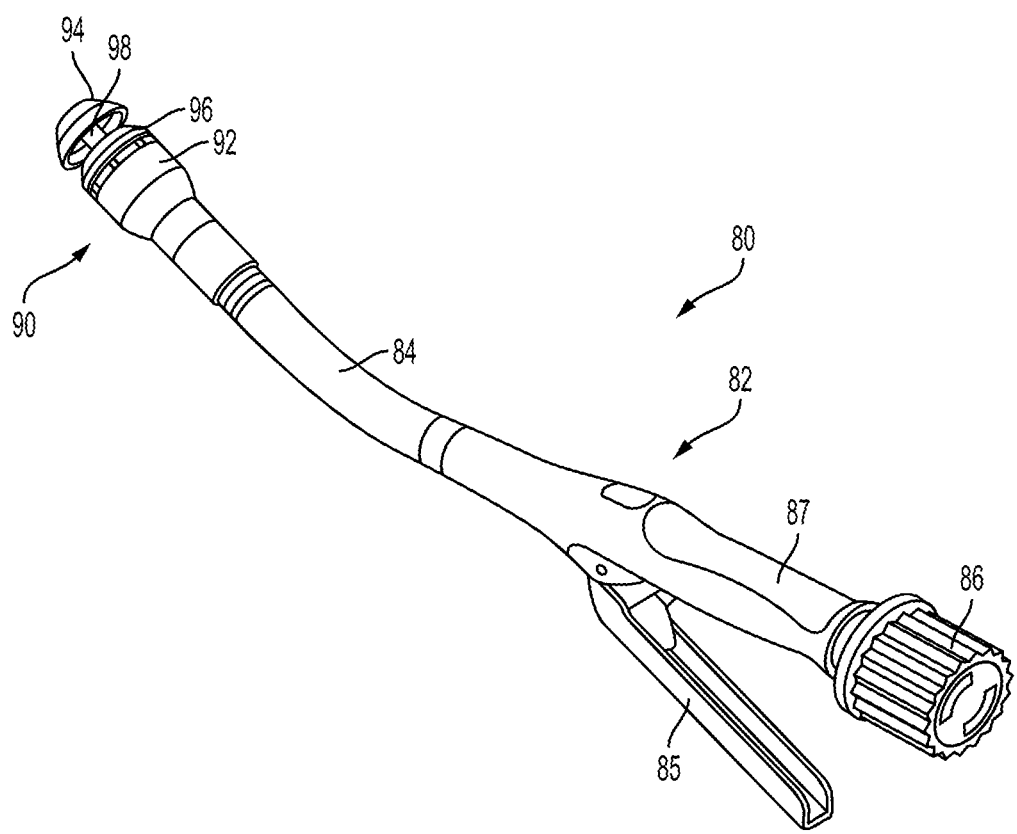
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076 entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or a combination of materials discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjuncts that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Implementations

Various exemplary devices, systems, and methods for releasably retaining an adjunct material on one or both jaws of an end effector of a surgical instrument are described herein. One or both of the opposed jaws can have retaining members formed thereon that are configured to mate with an adjunct material.

In some implementations, an adjunct material can be releasably retained on a jaw of an end effector in a secure manner, such that a possibility of the adjunct material prematurely slipping off the jaw is decreased or eliminated. In this way, the adjunct is securely coupled to the jaw while a surgeon manipulates the end effector during a surgical procedure. The adjunct remains coupled to the jaw until it is separated from the jaw and transferred to a treatment site in a patient, for example, when staples are deployed and/or when movement of a cutting element causes the adjunct to separate from the jaw. In such implementations, the adjunct material can be coupled to a jaw of an end effector using one or more contractible attachment features. The contractible attachment features, which are configured to couple the adjunct material with retaining members or other features of the jaw, can be features formed separately from the adjunct material. Additionally or alternatively, the contractible attachment features can be interwoven into or otherwise coupled to adjunct material.

In some embodiments, the contractible attachment feature can be in the form of one or more strands of a shrinkable polymer. The strands can be disposed on the adjunct material and/or they can be passed through the adjunct material in one or more locations. Furthermore, in some embodiments, the attachment feature can be in the form of a plurality of polymer strands interwoven into the adjunct material. The attachment features can be formed from any suitable material(s). For example, in some implementations, they can be formed from polydioxanone (PDO) or from other material(s) having a melting temperature that is lower than that of the adjunct material.

Regardless of the specific configuration of the contractible attachment features and the materials from which they are formed, each attachment feature can be configured to be transitioned from an original, non-contracted configuration to a contracted configuration under application of heat. The attachment feature can be engaged with the adjunct material, and contraction of the attachment feature is effective to couple the adjunct material with retaining members formed on the jaw. Adjunct materials can be releasably coupled to one or both jaws of an end effector of a surgical instrument using the contractible attachment features described herein.

Figure 6:
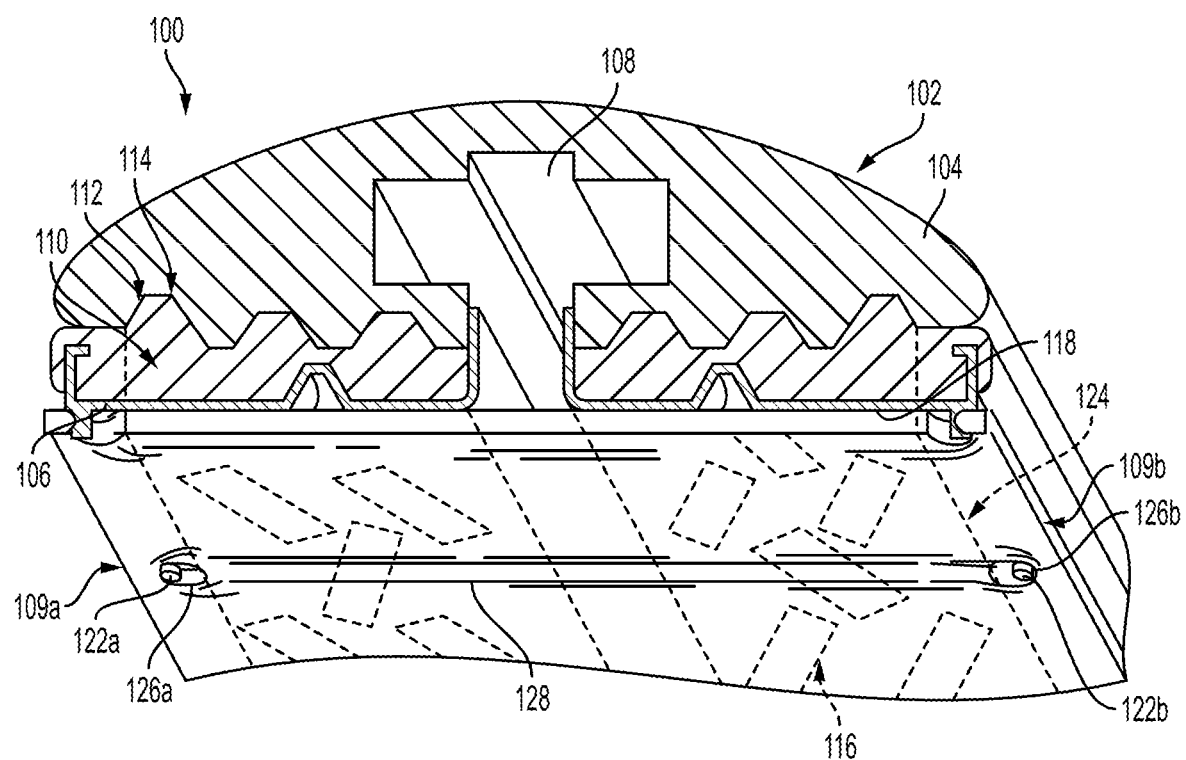
FIG. 6 is a perspective view of a jaw of an end effector that has an adjunct material releasably secured thereto.

FIG. 6 illustrates an example of a jaw of an end effector that has an adjunct material releasably secured thereto using contractible attachment features. FIG. 6 shows a portion of an end effector 100 of a surgical instrument configured to be coupled to a distal end of an elongate shaft of the surgical instrument (not shown). The end effector 100 can generally include components similar to those described with regard to FIGS. 1-4, and can also include features and/or components that enable adjuncts to be releasably attached thereto. Thus, similar to surgical staplers 10 (FIG. 1) and 50 (FIG. 4), the end effector 100 includes an upper jaw having an anvil and an lower jaw having a cartridge body (not shown), with only the upper jaw 102 being shown in FIG. 6. The lower jaw can generally include a staple cartridge that has a plurality of staple-holding cavities configured to seat staples therein, the staple-holding cavities opening on a tissue-facing surface of the cartridge.

As shown in FIG. 6, the upper jaw 102 having an anvil 104 can have an adjunct material 124 (shown partially transparent) releasably retained on a tissue-facing surface 118 of the anvil 104 using one or more contractible attachment features 128, as discussed in more detail below. As schematically shown in FIG. 6, the anvil 104 has staple-forming cavities 116 formed on the tissue-facing surface 118 thereof. As also shown, the tissue-facing surface 118 has a knife channel 108 configured to receive a cutting element (e.g., a knife) as it moves distally therethrough.

In the example illustrated, the anvil 104 is shown in the form of a modular jaw that includes an anvil plate 106 releasably attached to the anvil 104 via an adapter 110. The anvil plate 106 is a substantially rigid surface against which staples can be formed. In the illustrated example, the adapter 110 can include mating features 112 configured to mate with corresponding anvil features 114 formed along a side of the anvil 104 facing the opposed jaw, thereby ensuring an alignment between the anvil plate 106 and the cartridge-facing surface of the anvil 104. The adapter 110 can be, e.g., an elastomer or other compliant member, and it can be overmolded, adhered to, or otherwise coupled to the anvil plate. The adapter 110 can be used to releasably couple the anvil plate 106 to the anvil 104 in a variety of ways. For example, the adapter 110 can snap into the jaw 102. The modular configuration can allow interchangeably using anvil plates having different staple-forming features with the same jaw. The described techniques can be used in conjunction with various end effectors having modular jaws. For example, such end effectors are described in U.S. Patent Application No. [END8096USNP, 47364-244F01US] entitled "Surgical end effector adjunct attachment," filed on [even date therewith], and U.S. patent application Ser. No. 15/385,953 entitled "Methods of Stapling Tissue" filed on Dec. 21, 2016, the entire contents of which are incorporated by reference herein.

In the example of FIG. 6, the tissue-facing surface 118 is in the form of the surface of the anvil plate 106 facing the adjunct material 124. However, it should be appreciated that the modular anvil 104 having the anvil plate 106 is shown by way of example only, and that the described techniques can be used to releasably couple an adjunct material to any type of a jaw, including a jaw having a tissue-facing surface non-removably coupled thereto.

Regardless of its particular configuration, the tissue-facing surface 118 of the anvil 104 has at least first and second retaining members 122a, 122b that are configured to couple the adjunct material 124 to the anvil 104. The first retaining member 122a is disposed at one side of the tissue-facing surface 118 in proximity to one edge 109a of the tissue-facing surface 118, and the second retaining member 122b is disposed at another, opposed side of the tissue-facing surface 118 in proximity to another, opposed edge 109b thereof. In this way, the first and second retaining members 122a, 122b are disposed at opposed sides of the knife channel 108.

The retaining members 122a, 122b can have a variety of different configurations. In the example illustrated, they are in the form of generally cylindrical posts extending from the tissue-facing surface 118. However, the retaining members 122a, 122b can have other shapes, as the described implementations are not limited in this respect. For example, the retaining members can have an hour glass shape, a bulbous or widened end region, or any other shape. Additionally or alternatively, the retaining members can be curved and/or angled in any suitable manner. For example, as shown in FIG. 6, the retaining members 122a, 122b can be slightly angled away from one another towards respective edges 109a, 109b of the tissue-facing surface 118. Such configuration can assist in engaging the one or more attachment features 128 with the retaining members 122a, 122b, as discussed below. The retaining members can be configured in any other manner and have any other retaining features, such as, for example, one or more teeth, notches, grooves, undercuts, roughness areas, etc., that can facilitate retention of the attachment features 128 at the retaining members.

Although two retaining members 122a, 122b are shown in FIG. 6, the tissue-facing surface 118 can have any other number of retaining members (e.g., one or greater than two) configured to couple an adjunct thereto. Furthermore, the retaining members can be formed at various locations on the tissue-facing surface 118 of the anvil 104. For example, in some embodiments, two or more retaining members can be formed along each edge 109a, 109b of the tissue-facing surface 118. The retaining members can be formed at any suitable distance from one another that allows securely retaining the adjunct material on the jaw's tissue-facing surface. In addition, the retaining members can be disposed symmetrically with respect to the knife channel 108 or other features of the tissue-facing surface 118, or they can be formed at various other ways on the surface 118.

As shown in FIG. 6, in the example illustrated, each of the retaining members 122a, 122b is formed outside of the area of the tissue-facing surface 118 having the staple-forming cavities 116. However, in some implementations, one or more of the retaining members can be formed within the area having the staple-forming cavities 116.

As mentioned above, the adjunct material 124 is configured to releasably couple with the anvil 104 using at least one contractible attachment feature 128 configured to be transitioned from an original, non-contracted configuration to a contracted configuration under application of heat, as discussed in more detail below. The adjunct material 124 can couple with the anvil 104 in a secure manner, which helps ensure that the adjunct 124 remains coupled to the anvil 104 while the end effector 100 is manipulated as desired using a surgical procedure. The adjunct 124 is held in engagement with the anvil 104 until an action, such as an activation of the end effector 100 to release staples from its cartridge and/or an activation of a cutting element, is taken that causes the separation of the adjunct 124 from the anvil 104.

To accommodate a contraction of the at least one contractible attachment feature 128 that occurs as a result of heating, the adjunct material 124 can be configured such that it assumes an appropriate shape and size once heating has occurred so as to couple the adjunct material 124 to the jaw 102. For example, the adjunct material 124 can be sized such that it extends beyond the perimeter of the tissue-facing surface 118 of the anvil 104 prior to heating, and adopts the appropriate size once heating has occurred.

The first and second retaining members 122a, 122b are configured to mate with respective mating features of the adjunct material 124. In particular, in the described implementation, the adjunct material 124 includes openings 126a, 126b configured to receive the retaining members 122a, 122b, respectively. In this example, the through openings 126a, 126b in the adjunct 124 are generally round, though it should be appreciated that the openings 126a, 126b can have any other suitable shapes.

The openings 126a, 126b can have various sizes and configurations, and they can be disposed at various locations of the adjunct 124. For example, the openings 126a, 126b can be formed at locations of the adjunct material 124 that correspond to the locations of the retaining members 122a, 122b formed on the anvil plate 106.

In the described implementations, as mentioned above, the retaining members 122a, 122b couple the adjunct 124 to the anvil 104 by engaging one or more contractible attachment features 128 configured to be transitioned from an original, non-contracted configuration to a contracted configuration under application of heat. The contractible attachment features 128 can be in the form of one or more strands of a shrinkable polymer, which can be coupled to the adjunct material 124 at one or more locations. The adjunct material 124 and the at least one contractible attachment feature 128 can be made from a variety of materials. For example, in at least some embodiments, the adjunct 124 can be made from VICRYL® (polyglactin 910) material, whereas the contractible attachment feature 128 can be in the form of one or more PDO strands that can be bioabsorbable and/or biodegradable. Any other materials can be used additionally or alternatively. One or more of the strands can be coupled (e.g., removably) to the adjunct material 124. The PDO has a relatively low melting temperature, which is advantageous for its use in conjunction with adjuncts and attachment features. For example, the PDO has a melting temperature of 105 C.°. Heat can be applied for, for example, from 30 seconds to several minutes to cause the attachment feature 128 to transition into the contracted configuration.

Referring to FIG. 6, the contractible attachment features 128 can be engaged with the adjunct material, and contraction of the contractible attachment feature 128 is effective to couple the adjunct material 124 with the retaining members 122a, 122b. For example, the adjunct material 124 can be disposed over the tissue-facing surface 118 of the jaw 102 such that adjunct's openings 126a, 126b receive the retaining members 122a, 122b. In some embodiments, the adjunct material 124 can be applied to the jaw using a loader member, as discussed below. Further, the adjunct material 124 is associated with the at least one contractible attachment feature 128 which can be disposed over the adjunct material 124 such that the attachment feature 128 is engaged with the retaining members 122a, 122b. The attachment feature 128 can be coupled to the adjunct material 124—e.g., it can be in the form of one or more strands of a shrinkable polymer, one or more of which are passed through at least one portion of the adjunct 124. Heat can be applied to cause at least a portion of the attachment feature 128 to contract to thereby cause the adjunct material 124 to couple with the retaining members 122a, 122b using the attachment feature 128. In particular, the attachment feature 128 can be caused to transition from the original, non-contracted configuration to the contracted configuration such that, in the contracted configuration, the attachment feature 128 is coupled to retaining members 122a, 122b and thereby retains the adjunct material 124 in secure (albeit releasable) engagement with the retaining members 122a, 122b and thus with the anvil 104.

It should be appreciated that the adjunct materials can be attached to an end effector using various other approaches. For example, the U.S. patent application Ser. No. 14/871,078 entitled "Tubular Absorbable Constructs" filed on Sep. 30, 2015, which is incorporated by reference herein in its entirety, describes another approach.

Figure 7A:
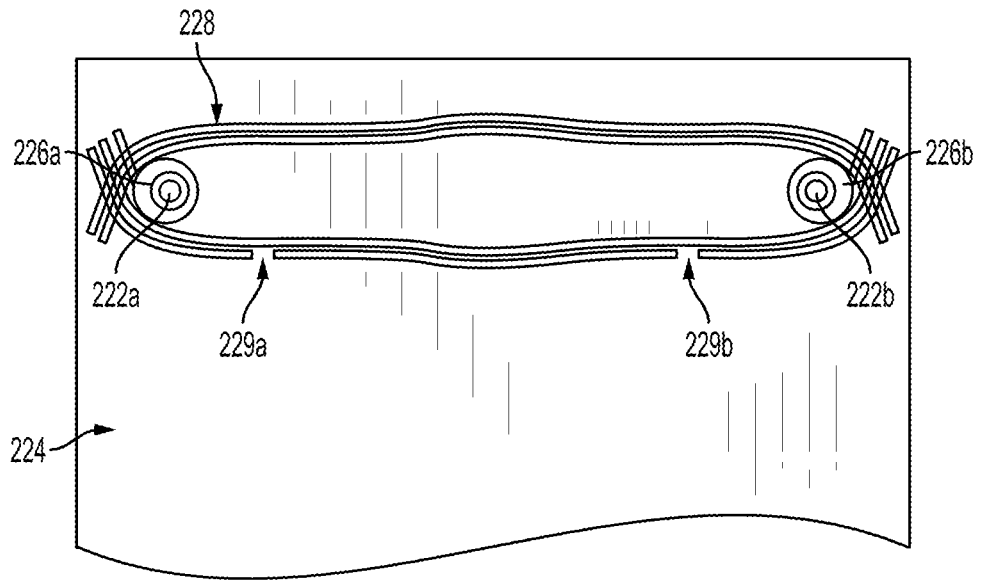
FIG. 7A is a perspective view an adjunct that has contractible attachment features disposed on a jaw of an end effector before the adjunct is coupled to the jaw.
Figure 7B:
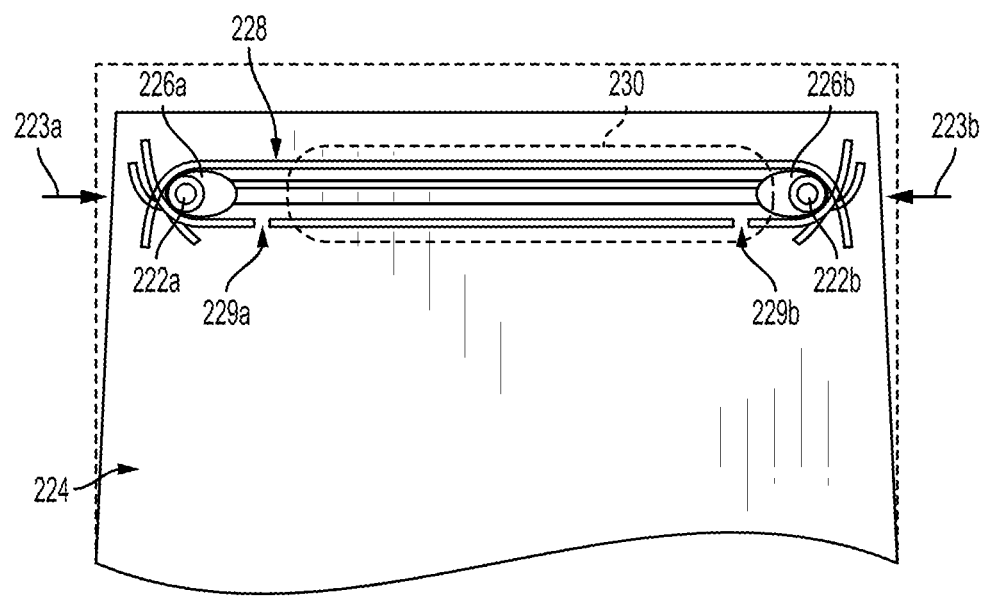
FIG. 7B is a perspective view of the adjunct of FIG. 7A, illustrating the adjunct coupled to the jaw by application of heat.

FIGS. 7A and 7B illustrate an embodiment of an adjunct material or adjunct 224 that can be disposed on a tissue facing surface of a jaw (not shown), such as a jaw having an anvil (e.g., anvil 104 in FIG. 6). It should be appreciated that the jaw can also be a jaw having a cartridge. In this example, the adjunct 224 has a plurality of attachment features 228 associated therewith.

The attachment features 228 can be in the form of two or more attachment features. The attachment features 228 can be, for example, strands of a shrinkable polymer, such as PDO strands that can pass through at least one portion of the adjunct material, at one or more points. For example, the PDO strands can be woven, knitted, braded into the adjunct 224, or otherwise associated with the adjunct 224. As shown by way of example, one or more of the attachment features 228 can be coupled to the adjunct 224 at points 229a, 229b, though it should be appreciated that the attachment feature 228 can be coupled to the adjunct 224 at any number of points at any locations in the adjunct 224. In some cases, the adjunct 224 can be manufactured such that the attachment features 228 are created during the manufacturing process and are thus part of the adjunct 224. In other embodiments, however, some or all of the attachment features 228 can be separate threads coupled to the adjunct 224.

In use, the adjunct 224 can be mated with the jaw via retaining members 222a, 222b formed on the jaw and mating with openings 226a, 226b in the adjunct 224. As shown in FIG. 7A, before the adjunct 224 is securely and releasably coupled to the jaw, the attachment features 228 are in a non-contracted configuration such that they form one or more loops that encompass both of the retaining members 222a, 222b. As shown, the loops can be disposed in a relatively loose manner around the retaining members 222a, 222b. As discussed above, the attachment features 228 can be associated with the adjunct in a variety of ways. For example, they can be passed through one or more portions of the adjunct 224. Additionally or alternatively, the attachment features can be disposed over, and coupled to the adjunct using, e.g., an adhesive.

As illustrated schematically in FIG. 7B, the adjunct 224 can be secured to the jaw by applying heat to a region 230 that encompasses a portion of the attachment features 228. Under the application of heat, the attachment features 228 transition from the non-contracted configuration (shown in FIG. 7A) to a contracted configuration as shown in FIG. 7B. In the contracted configuration, the attachment features 228 can be arranged such that one or more loops are engaged around the retaining members 222a, 222b and thereby releasably retain the adjunct material 224 over the jaw. In this way, in the contracted configuration, the loops of the attachment features 228 are held in tension more tightly around the retaining members 222a, 222b than in the non-contracted configuration. Also, as mentioned above, the retaining members 222a, 222b are configured to have retaining features that facilitate engagement of the attachment features 228 therewith.

In the example shown in FIG. 7B, when heat is applied to a region encompassing a portion of the attachment features 228, the portions of the attachment features 228 in that region contract. The heat can be applied to the attachment features 228 in a variety of ways, as discussed in more detail below. The contraction results in the attachment features 228 and the through openings 226a, 226b being tensioned around the retaining members 222a, 222b which thus releasably retain the adjunct 224 over the jaw. Thus, FIGS. 7A and 7B illustrate that the area of the adjunct 224 is reduced to some degree after the heat has been applied. FIGS. 7A and 7B also illustrate that a shape of the openings 226a, 226b formed the adjunct 224 changes when the adjunct 224 is in the contracted configuration. In particular, the openings 226a, 226b become more stretched as the material from which the adjunct 224 is formed as pulled towards the middle of the adjunct 224 due to the contraction of the attachment features 228, which is also shown by arrows 223a, 223b in FIG. 7B. When the staples are fired and a cutting element (e.g., a knife) is activated, the attachment features 228 are cut, thus allowing the adjunct 224 to separate from the jaw.

It should be appreciated that the implementation in FIGS. 7A and 7B is shown by way of example only. Thus, the attachment features 228 can be wrapped around the retaining members in many various ways. For example, as in the example illustrated, the attachment features 228 can form one or more loops in a substantially oval pattern. As another example, the attachment features can be arranged in a figure-eight pattern around the retaining members, or they can be arranged such that one or more portions form one or more crisscross patterns over the adjunct. Also, the attachment feature(s) can be arranged around the retaining members in a substantially random way. As mentioned above, one or more of the attachment features can be coupled to (e.g., woven through) the adjunct at one or more locations. Moreover, in some implementations, one or more of the attachment features can be coupled to or interconnected with one another.

Furthermore, in some embodiments, the attachment features are not engaged with the retaining members. For example, the adjunct can have openings formed around its perimeter some or all of which can be engaged with (e.g., receive therethrough) the retaining members of the jaw. The contractible attachment features, which can be coupled to the adjunct in any suitable manner (e.g., passed through the adjunct one or more times, attached used an adhesive, etc.), can be disposed in a certain way, e.g., across the middle of the adjunct, such that, when they are exposed to heat, they constrict and cause the two sides of the adjunct to be pulled together. Depending on the configuration of the adjunct and the attachment features, the adjunct will constrict or deform as a result of the application of heat in a suitable manner.

In the example shown in FIGS. 7A and 7B, the adjunct 224 is secured to the tissue-facing surface of the jaw using multiple attachment features 228. However, in some embodiments, a single continuous attachment feature can be used to secure an adjunct to a jaw of an end effector. Such embodiments can be used, for example, if limited interconnection between the adjunct and the attachment feature is desired. In other words, the attachment feature can be coupled to the adjunct in fewer locations as compared to implementations in which two or more attachment features are used.

Figure 8A:
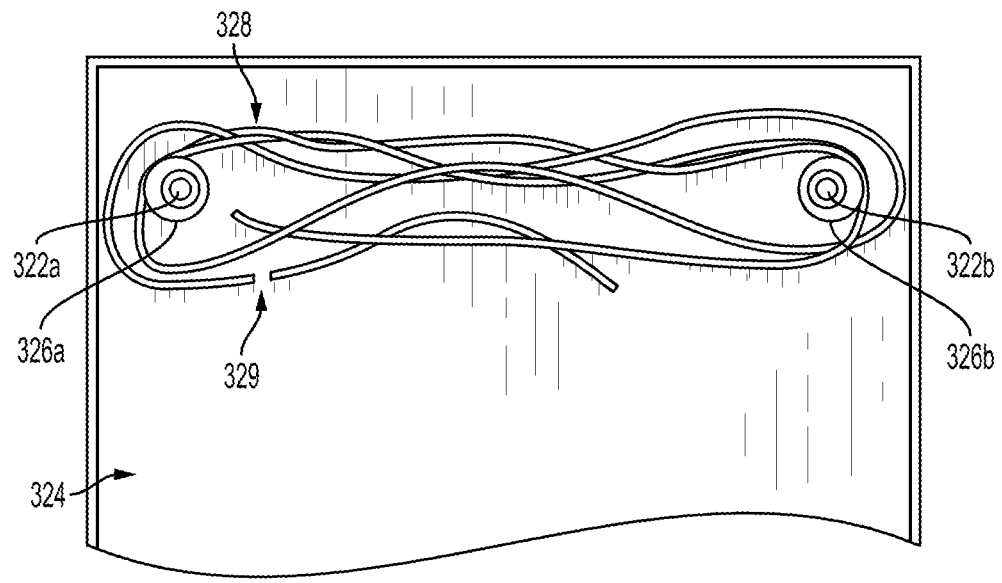
FIG. 8A is another perspective view an adjunct that has contractible attachment features disposed on a jaw of an end effector before the adjunct is coupled to the jaw.
Figure 8B:
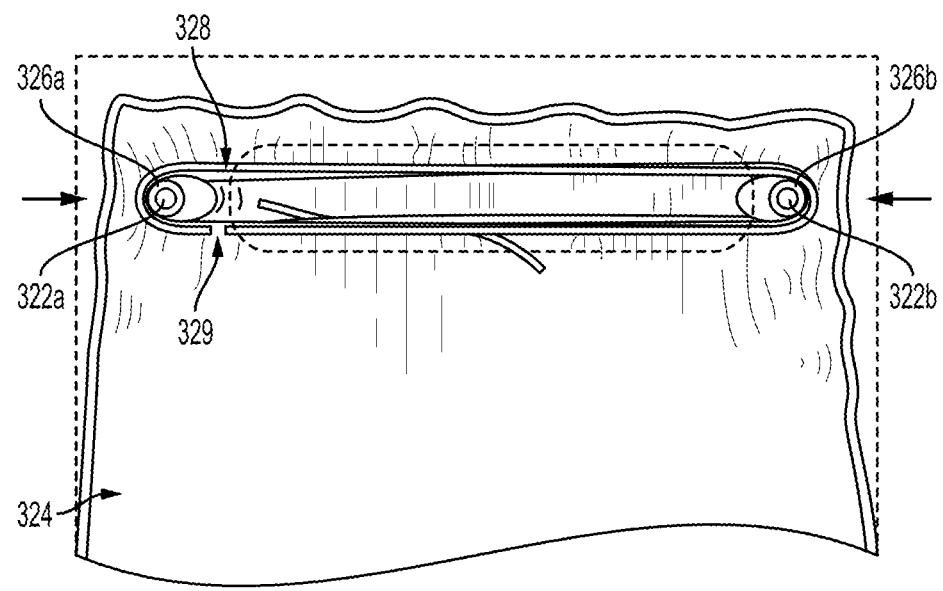
FIG. 8B is a perspective view of the adjunct of FIG. 8A, illustrating the adjunct coupled to the jaw by application of heat.

FIGS. 8A and 8B illustrate an embodiment in which a continuous attachment feature 328 is used to couple an adjunct material or adjunct 324 to a jaw (not shown), such as a jaw having an anvil (e.g., anvil 104 in FIG. 6) or a jaw having a cartridge. In this example, the attachment feature 328 is a relatively long continuous feature disposed over a portion of the adjunct 324 as shown in FIG. 8A.

As shown, the adjunct 324 is disposed over the jaw such that retaining members 322a, 322b formed on the jaw are mated with through openings 326a, 326b in the adjunct 324. As also shown, the attachment feature 328 can form one or more loops that encompass the retaining members 322a, 322b. As shown by way of example, the attachment feature 328 can be coupled to the adjunct 324 at a point 329, though it should be appreciated that the attachment feature 328 can be coupled to the adjunct 324 at any number of points at any locations of the adjunct 324. The attachment feature 328 can be woven into, knitted through, stitched through, or otherwise coupled to the adjunct 324. In addition, in some embodiments, one or more portions of the attachment feature 328 can be coupled one another, e.g., using an adhesive. Additionally or alternatively, some of the portions can be tied, twisted, bonded together, etc.

In the example illustrated, as shown in FIG. 8B, when heat is applied to a region 330 encompassing a portion of the attachment feature 328, one or more portions of the attachment feature 328 contract. As the contraction occurs, the attachment feature 328 is brought closer towards the retaining members 322a, 322b such that the material of the attachment feature 328 engages more tightly around the retaining members 322a, 322b, thereby releasably retaining the adjunct 324 over the jaw. In other words, the attachment feature 328 is held in tension around the retaining members 322a, 322b. When the staples are fired and a cutting element (e.g., a knife) is activated, the attachment feature 328 is cut to thus allow the adjunct 324 to separate from the jaw.

In this way, FIGS. 7A, 7B, 8A, and 8B illustrate that the adjuncts 224, 324 can be securely coupled to a jaw in a manner than allows manipulating the jaw as desired during a surgical procedure. A risk of the adjunct slipping off or otherwise being unintentionally and prematurely separated from the jaw is reduced or eliminated.

In the examples of FIGS. 7A, 7B, 8A, and 8B, the attachment features can be formed from any suitable materials. For example, they can be in the form of one or more PDO strands. A density of the PDO strands can vary throughout the attachment features and thus throughout the adjunct to which the feature(s) are attached. In this way, the degree of contraction of the attachment feature(s) varies in different parts of the adjunct. In some cases, elongate PDO strands can be woven throughout the entire adjunct such that more uniform adjunct contraction can be achieved. The PDO strands can also be wrapped around the retaining members to ensure that they effectively engage the retaining members when heat is applied and contraction occurs. As another example, the attachment features can be separate from the adjunct. In such cases, upon heating, the attachment features contract, and become secured in tension between the retaining members, thereby holding the adjunct in place, but the contraction of the attachment features may not have an impact on the configuration of the adjunct. Alternatively, as discussed above, the attachment features can be attached to the adjunct at certain attachment points, which can be based on the desired configuration of the adjunct and the amount of contraction.

Figure 9A:
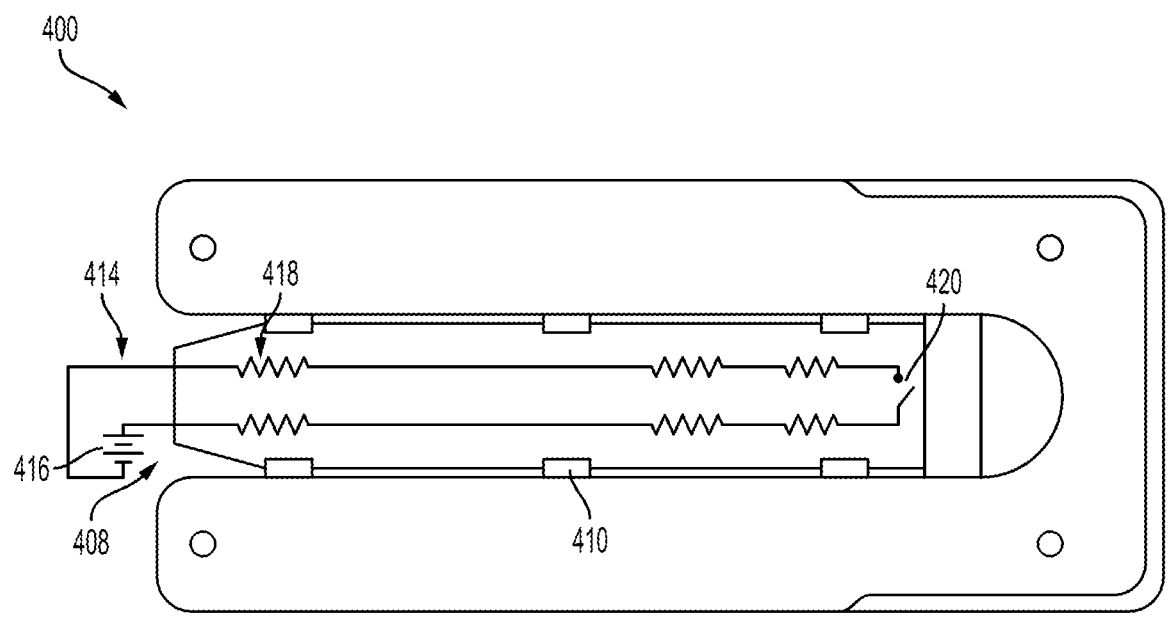
FIG. 9A is a top view of one embodiment of a loader.
Figure 9B:
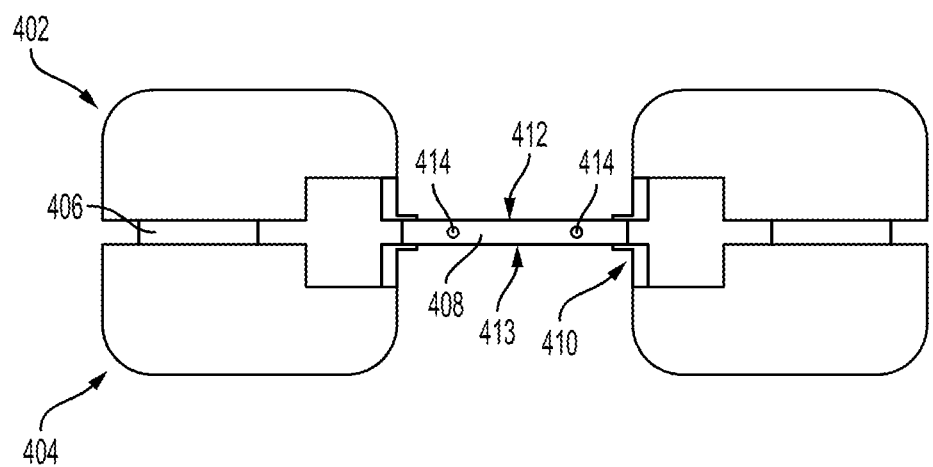
FIG. 9B is a cross-sectional view of the loader of FIG. 9A.

In the described embodiments, one or more attachment features can be used to releasably engage an adjunct with a jaw of an end effector using heat. The heat can be applied in a variety of ways. For example, in some embodiments, heat can be applied using a loader that is configured to apply the adjunct to the jaw. FIGS. 9A and 9B illustrate an example of a loader 400 configured to apply an adjunct to a tissue-facing surface of a jaw. FIG. 9A shows a top view of the loader 400, whereas FIG. 9B shows a cross-sectional view of the loader 400.

As in the illustrated example, the loader 400 in the form of a generally rectangular frame-like holder configured to releasably couple one or more adjuncts to one or both jaws of the end effector (not shown). In the illustrated example, the loader 400 is in the form of a first (e.g., top) and second (e.g., bottom) generally rectangular housings 402, 404 coupled to one another e.g., via a coupling 406, as shown in FIG. 9B. In this example, the loader 400 can be used to apply a single adjunct to a jaw. It should be appreciated however, that, in some embodiments, a loader like the loader 400 or a similar loader, can be used to apply a respective adjunct to each jaw of an end effector.

The loader 400 includes at least one heating component 408 configured to be activated to apply heat to attachment features, as described below. The heating component 408 can have various configurations. For example, as shown in FIGS. 9A and 9B, the heating component 408 includes a resistive heating element 414 in the form of a wire. The heating element 414 is connected to a power source 416. In the illustrated example, the heating element 414 includes higher resistance portions 418 along its length. The locations of the higher resistance portions 418 can correspond to regions on an adjunct to which heat is desired to be applied, e.g. region 230 (FIG. 7B) or region 330 (FIG. 8B). Thus, power can be applied to the heating element 414 to cause localized heating near the higher resistance portions 418. In some embodiments the heating element can include a switch 420 that closes the circuit and allows current to flow through the heating element. The switch 420 can be operated using a suitable trigger on the loader 400 (e.g., a button), though the heating element 414 can be activated in other suitable ways. The heat generated by the higher resistance portions 418 causes the attachment features that are engaged with the adjunct to contract to effectively couple the adjunct with retaining members of the jaw, thereby releasably retaining the adjunct over the tissue-facing surface of the jaw.

The heating component 408 can be of any suitable type. For example, the heating component 408 can be made of a rigid material, e.g., ceramic, that is coated with an elastic or compliant material. In some embodiments, the heating component 408 can be in the form of a resistive wire embedded into silicone, e.g., such that the silicone is cured around the resistive wire. The resistive wire is configured to effect the heating, whereas the silicone allows for some degree of compliance when clamping a stapler onto the loader. As shown in FIG. 9B, the heating component 408 can be coupled to the housings 402, 404 via connecting features 410, e.g., brackets.

The loader 400 and heating component 408 can generally be configured such that an adjunct (not shown) can be placed on a surface, e.g., an upward facing surface 412 of the heating component as shown in FIG. 9B, and the jaws of the end effector can clamp over the heating component and adjunct. Although not illustrated, the loader 400 and/or heating component 408 can include retaining features that can releasably secure adjuncts to surfaces 412 and 413 such that the adjuncts can be secured to both jaws of an end effector simultaneously. For example, the heating component 408 can have small posts or hooks that can grip the adjuncts to releasably secure them to surfaces 412, 413. In one embodiment, the heating component 408 is disposable and it is coupled to adjuncts secured to the surfaces 412, 413. In such an embodiment, the loader 400 is configured to receive a heating component 408 with adjuncts attached thereto. The surgeon can load the heating component 408 with the adjuncts into the loader 400, and attach the adjuncts to jaws of an end effector.

Furthermore, in some embodiments, the heating component 408 (or a heating component having another configuration) can be in the form of two heating components disposed in the removable loader such that each of the heating components is configured to apply heat to a different adjunct that can be associated therewith (e.g., via the loader or manually). In such implementations, with reference to FIG. 9B, for example, first and second adjuncts are placed on the surfaces 412, 413, respectively, and heat can be applied to the adjuncts using respective heating components associated with the surfaces 412, 413.

Regardless of the specific way in which the heating component 408 is associated with the loader 400, the loader 400 can be used to both deliver the adjunct to the jaw (such that the adjunct is transferred from the loader to the jaw) and to apply heat to the adjunct. In use, the loader can be placed between the jaws of the end effector that are in an open configuration. The jaws can then be clamped over the loader 400 to thereby clamp over the heating component 408 and the adjunct such that the adjunct is transferred onto the jaw and retaining members on the jaw enter through openings on the adjunct, as illustrated, e.g., in FIGS. 7A and 8A. At least one attachment feature can be engaged with the adjunct, e.g., as shown for attachment features 228, 328 and adjuncts 224, 324 in FIGS. 7A and 8A, respectively. The heating element 414 can be activated in a suitable manner such that heat applied therefrom to the at least one attachment feature can cause the attachment feature to contract, which causes the adjunct material to couple with the first and second retaining members.

In some embodiments, the act of clamping the jaws onto the heating component closes the switch 420, thereby allowing current to flow through the heating element. Once the adjunct is secured to the jaw as desired, the jaws can be opened and removed from the heating component which allows the switch 420 to open, thereby stopping the flow of current within the heating element 414.

In other implementations, an adjunct may not be associated with a loader, such as the loader 400, and the loader can be used only to apply heat to the adjunct (and thus to at least one attachment features). In such implementations, an adjunct is placed onto a tissue-facing surface of a jaw, and attachment features engaged with or disposed over the adjunct is looped around jaw's retaining members as desired to loosely secure the adjunct to the end effector. The end effector is then be clamped onto the loader with the heating component 408 of the loader 400, and the heating element 414 is powered, thereby causing localized heating near the high resistance portions 418 of the heating element 414. The heat from those portions 418 causes the attachment features that are engaged with the adjunct to contract to effectively couple the adjunct with the retaining members, thereby releasably retaining the adjunct over the tissue-facing surface of the jaw.

It should be appreciated that the loader 400 is shown by way of example only. In some embodiments, a loader can use a chemical reaction to supply heat to the attachment features. For example, the loader can generally be similar to loader 400, but rather than using a heating component that includes a resistive heating element, the loader can use a heating component including one or more fluid or crystalline structures. By way of example, the heating element can include a number of fluid or crystalline structures that can release heat when they come in contact with each other. In some implementations clamping jaws of an end effector onto the heating component can cause internal pockets containing fluid or crystalline structures to crack, thereby allowing their internal substances to combine. When the substances combine, the mixture undergoes an exothermal chemical reaction that releases heat. The heating component can be configured such that the chemical heating elements are in the desired locations, and wherein cracking the heating elements only breaks an internal barrier and does not cause the substances to spill from the heating component.

Furthermore, in some embodiments, heat can be applied to an adjunct with at least one attachment feature pre-loaded thereon using a device different from a loader. For example, the adjunct can be disposed on a jaw of an end effector and heat can be applied thereto using an infrared heater, UV heater, heat gun, or any other device configured to provide heat. In some cases, the heating can be done by placing the end effector with the adjunct disposed thereon in a suitable oven, heated chamber, or other enclosure configured to apply heat. The separate heating devices can be used in embodiments in which the adjunct is pre-applied to the end effector's jaws during manufacture of the end effector. The loader, such as the loader 400, or a similar applicator (e.g., a small heating chamber) can be used in embodiments in which the adjunct is configured to be applied in the operating room by the surgeon or other person during or before a surgical procedure.

Regardless of the way in which heat is applied to the adjunct, a temperature of the heat and a duration of its application is selected so as to cause at least one attachment feature to contract and thus cause the adjunct to be attached to the jaw. For example, the heat can have a temperature of from about 100 to about 130 degrees Celsius and it can be applied for, for example, from about 20 seconds to about 3 minutes to cause the attachment feature to transition into the contracted configuration. It should be appreciated, however, that a temperature in other ranges can be applied for any suitable time period.

Figure 10A:
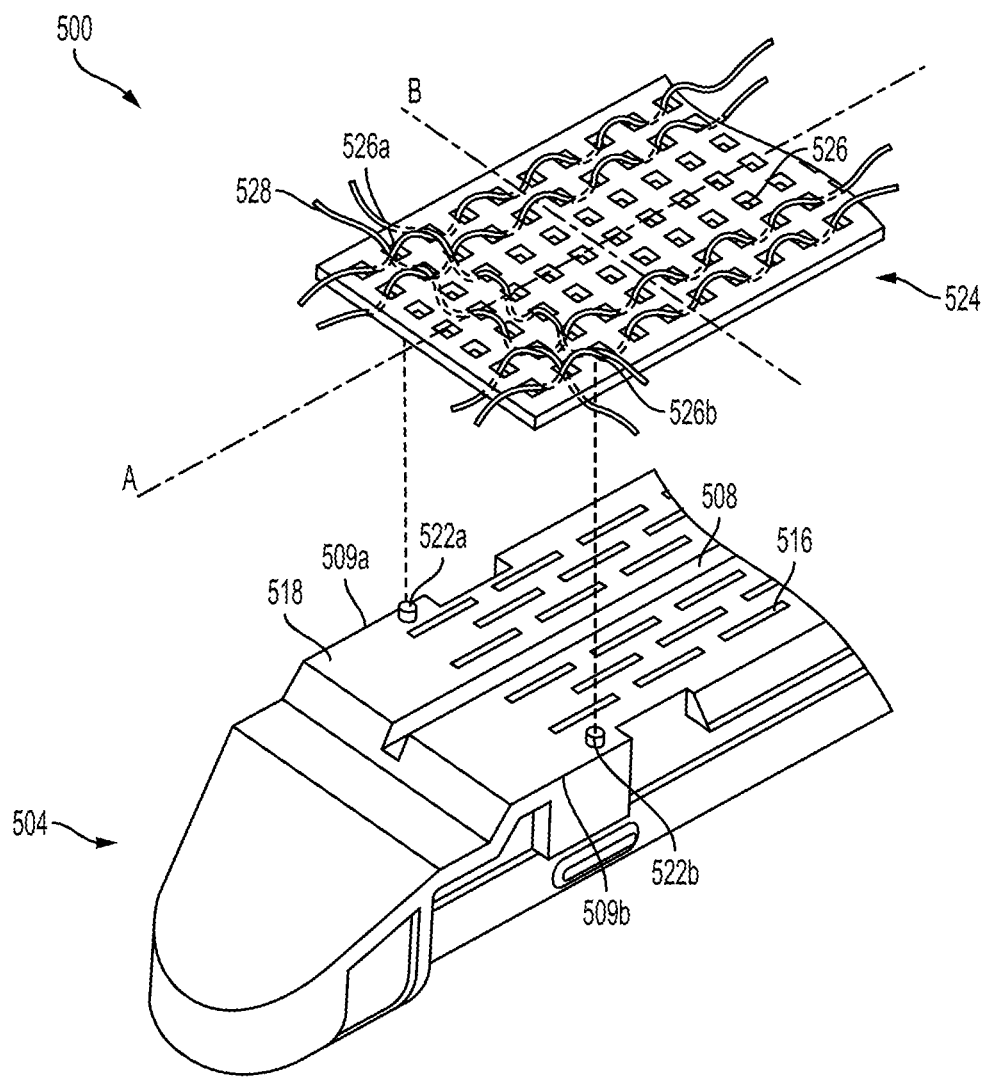
FIG. 10A is a perspective view of a jaw and an adjunct configured to be releasably coupled to the jaw.
Figure 10B:
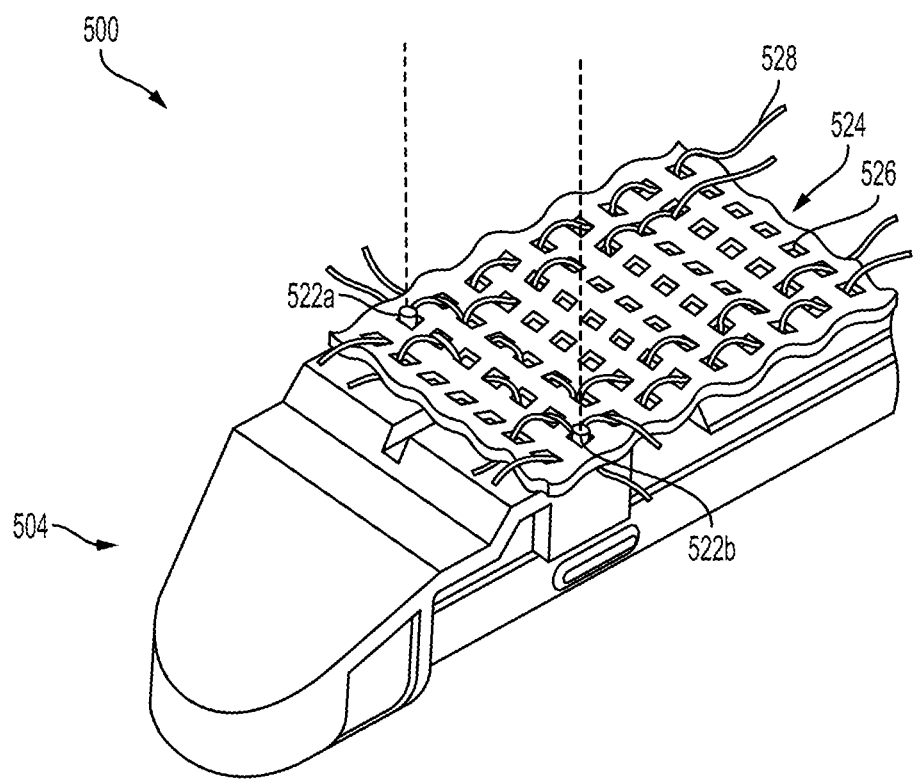
FIG. 10B is a perspective view of the jaw of FIG. 10A, illustrating the adjunct releasably coupled to the jaw.

In some applications, an adjunct can be formed such that a plurality of contractible attachment features are interwoven into the adjunct along a longitudinal axis of the adjunct and along an axis that is substantially perpendicular to the longitudinal axis of the adjunct. FIGS. 10A and 10B illustrate an example of such an adjunct. In particular, FIGS. 10A and 10B illustrate a portion of an end effector 500 that is configured to have an adjunct 524 coupled to a tissue-facing 518 surface of a jaw, wherein the adjunct 524 has contractible attachment features 528 interwoven with the adjunct 524 along a longitudinal axis A and along a lateral axis B that is substantially perpendicular to the longitudinal axis A.

The end effector 500 can generally include components similar to those described with regard to end effector 100 (FIG. 6). Thus, similar to the end effector 100, the end effector 500 can include an upper jaw (not shown) having an anvil and a lower jaw having a cartridge body 504. The lower jaw includes the staple cartridge 504 that has a plurality of staple-holding cavities 516 configured to seat staples therein, the staple-holding cavities 504 opening on a tissue-facing surface 518 of the cartridge 504. The staple cavities can form a certain pattern on the tissue-facing surface 518 of the cartridge 504 which corresponds to a pattern of staple-forming cavities formed in the anvil. The cartridge 504 includes first and second retaining members 522*a*, 522*b*, located adjacent to opposed edges of the tissue-facing surface 518, and a knife channel 508 extending between distal and proximal ends of the cartridge 504.

The retaining members 522*a*, 522*b* disposed on the tissue-facing surface 518 of the cartridge 504 are configured to releasably couple an adjunct material 524 to the cartridge 504. The first retaining member 522*a* is disposed at one side of the tissue-facing surface 518 in proximity to one edge 509*a* of the tissue-facing surface 518, and the second retaining member 522*b* is disposed at another, opposed side of the tissue-facing surface 518 in proximity to another, opposed edge 509*b* thereof. In this way, the first and second retaining members 522*a*, 522*b* are disposed at opposed sides of the knife channel 508.

The retaining members 522*a*, 522*b* can have a variety of different configurations. In the example illustrated, they are in the form of generally cylindrical posts extending from the tissue-facing surface 518. However, the retaining members 522*a*, 522*b* can have other shapes, as the described implementations are not limited in this respect. For example, the retaining members 522*a*, 522*b* can be curved, have an hour glass shape, have a bulbous or widened end region, have notches, be angled toward the edges of the tissue-facing surface, have roughness features, etc. The retaining members can be configured in any manner suitable for assisting in retaining the adjunct on the jaw. Also, although two retaining members 522a, 522b are shown in FIG. 10A, the tissue-facing surface 518 can have any other number of retaining members (e.g., one or greater than two) configured to couple an adjunct thereto. Furthermore, the retaining members can be formed at various locations on the tissue-facing surface 518 of the cartridge 504. For example, in some embodiments, two or more retaining members can be formed along each edge 509a, 509b of the tissue-facing surface 518. The retaining members can be formed at any suitable distance from one another that allows securely retaining the adjunct material on the jaw's tissue-facing surface. In addition, although in the illustrated implementations the retaining members protrude above the surface of the tissue-facing surface, in some embodiments, the retaining members can be in the form of recesses or other features disposed at least partially below the tissue-facing surface of the jaw. This can be done in implementations in which a reload includes reverse drivers.

As shown in FIG. 10A, in the example illustrated, each of the retaining members 522a, 522b is formed outside of the area of the tissue-facing surface 518 having the staple cavities 516. However, in some implementations, one or more of the retaining members can be formed within the area having the staple cavities 516.

The adjunct material 524 is configured to releasably couple with the cartridge 504 using a plurality attachment features 528 configured to be transitioned from an original, non-contracted configuration to a contracted configuration under application of heat, as discussed in more detail below. The adjunct material 524 couples with the cartridge 504 in a secure manner, which helps ensure that the adjunct 524 remains coupled to the cartridge 504 while the end effector 500 is manipulated as desired using a surgical procedure. The adjunct 524 is held in engagement with the cartridge 504 until an action, such as an activation of the end effector 500 to release staples from its cartridge and/or an activation of a cutting element, is taken that causes the separation of the adjunct 524 from the cartridge 504.

To accommodate a contraction of the at least one attachment feature 528 that occurs as a result of heating, the adjunct material 524 can be configured such that it assumes an appropriate shape and size once heating has occurred so as to couple the adjunct material 524 to the cartridge 504. For example, the adjunct material 524 can be sized such that it extends beyond the perimeter of the tissue-facing surface 518 of the cartridge 504 prior to heating, and adopts the appropriate size once heating has occurred.

The first and second retaining members 522a, 522b are configured to mate with respective mating features of the adjunct material 524. In particular, in the described implementation, the adjunct material 524 includes a plurality of through openings 526, wherein at least first and second openings 526a, 526b of the openings 526 are configured to be mated with the retaining members 522a, 522b. It should be appreciated that, depending on the number of the retaining members, more than two of the openings 526 can mate with respective retaining members.

The openings 526 in the adjunct 524 can have any suitable size and shape, including different sizes and shapes. In this example, the openings 526 are generally square, though it should be appreciated that the openings 526 can have any other suitable shapes. In the illustrated example, the attachment features 528 can be woven through the openings 526 as shown in FIGS. 10A and 10B. Also, the openings 526 can also be positioned and dimensioned to control the configuration of the adjunct and internal stress imposed upon the adjunct when heat is applied and the attachment features contract. The openings can be formed in the adjunct such that specific openings (e.g., openings 526a, 526b) are configured to receive corresponding retaining members. Alternatively, in some cases, when the adjunct is disposed over the jaw, the openings in the adjunct can "find" retaining members to mate with, and it may therefore not be necessary to make openings that specifically correspond to positions of the retaining members.

The contractible attachment features 528 can be in the form of one or more strands of a shrinkable polymer, which can be coupled to the adjunct material 524 at one or more locations. The adjunct 524 can have any suitable number of attachment features interwoven into the adjunct 524 such that at least one attachment feature is disposed along the longitudinal axis A and at least one attachment feature is disposed along the lateral axis B. In the example of FIG. 10A, fours strands of shrinkable polymer are disposed along the longitudinal axis A of the adjunct 524 (two along each of the long sides) and two strands of shrinkable polymer are disposed along the lateral axis B of the adjunct 524 (closer to the distal end of the jaw 504). However, it should be appreciated that the attachment features 528 can be in the form of any suitable number of strands that can be coupled to the adjunct 524 in any desired manner. For example, in one embodiment, one or more of the stands can be coupled to the adjunct 524 so as to be diagonally disposed with respect to the adjunct 524. The strands can be coupled to the adjunct to be able to contract in a way so as to transition one or more portions of adjunct to a desirable shape and size. For example, the strands must be able to cause some of the openings in the adjunct to constrictably engage with the retaining members. In some cases, the same strand can be interwoven into the adjunct along the longitudinal axis A as well as the lateral axis B.

The adjunct material 524 and the at least one contractible attachment feature 528 can be made from a variety of materials. For example, in at least some embodiments, the adjunct 524 can be made from VICRYL® (polyglactin 910) material, whereas the contractible attachment feature 128 can be in the form of one or more PDO strands. Any other materials can be used additionally or alternatively.

In the described implementations, the retaining members 522a, 522b couple the adjunct 524 to the cartridge 504 by mating with two corresponding openings 526a, 526b. When heat is applied, the attachment features transition from a non-contracted configuration to a contracted configuration and thereby causing the at least the openings 526a, 526b to constrict around the retaining members 522a, 522b, as shown schematically in FIG. 10B. Thus, in the contracted configuration, the attachment features 528 are coupled to the retaining members 522a, 522b or cause the adjunct 524 to couple to the retaining members 522a, 522b. In this way, the adjunct material 524 is retained in a secure and releasable engagement with the retaining members 522a, 522b and thus with the cartridge 504, as illustrated in FIG. 10B. Heat can be applied to the adjunct 524 with the attachment feature 528 using a variety of techniques, as discussed above. For example, loader 400 (FIGS. 9A and 9B), or any other device configured to provide heat can be used.

In the examples described above, an adjunct can be attached to a cartridge and/or anvil during manufacturing, or by a surgeon before or during a surgical procedure. The adjunct can be secured to the end effector using one or more shrinkable attachment features that can change their configuration under application of heat. In other embodiments, however, the adjunct can be releasably coupled to the jaw using other approaches that do not require application of heat.

Thus, in some embodiments, at least one first portion of an adjunct material or adjunct is configured to be reversibly stretched by an application of force. When the force is removed, the first portion transitions from a stretched configuration to a contracted configuration, thereby causing the adjunct material to engage a jaw of an end effector. The jaw can have one or more retaining features configured to mate with corresponding features of the adjunct. For example, first and second retaining features formed on the jaw can mate with mating features (e.g., openings) of the adjunct. Thus, the at least partially stretchable adjunct material (or portion(s) thereof) can be stretched and then allowed to contract, which causes the adjunct's mating features to engage the jaw's retaining features. In some embodiments, the adjunct can have one or more portions that are substantially non-stretchable.

Figure 11:
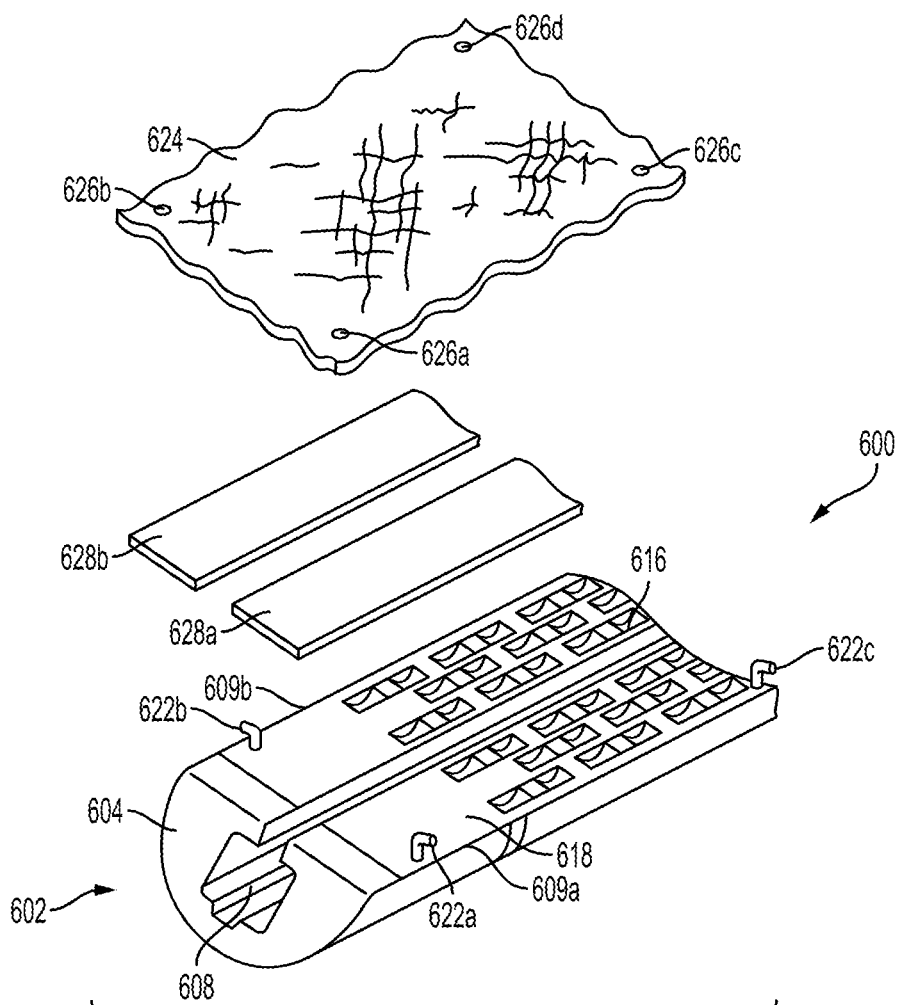
FIG. 11 is an exploded view of a jaw of an end effector and at least partially stretchable adjunct material configured to be releasably coupled to the jaw.

FIG. 11 illustrates an exploded view of an example of a jaw 602 of an end effector 600 of a surgical instrument that has an adjunct material releasably secured thereto using an approach that does not depend on application of heat. The end effector 600 can generally include components similar to those described with regard to FIGS. 1-4, and can also include features and/or components that enable adjuncts to be releasably attached thereto. Thus, similar to surgical staplers 10 (FIG. 1) and 50 (FIG. 4), the end effector 600 includes an upper jaw having an anvil and an lower jaw having a cartridge body (not shown), with only the upper jaw 602 being shown in FIG. 11. The lower jaw can generally include a staple cartridge that has a plurality of staple-holding cavities configured to seat staples therein, the staple-holding cavities opening on a tissue-facing surface of the cartridge.

As shown in FIG. 11, the upper jaw 602 having an anvil 604 has an adjunct material 624 releasably retained on a tissue-facing surface 618 thereof, as discussed in more detail below. The anvil 604 has staple-forming cavities 616 formed on the tissue-facing surface 618. As also shown, the tissue-facing surface 618 has a knife channel 608 configured to receive a cutting element (e.g., a knife).

As shown in FIG. 11, the tissue-facing surface 618 of the anvil 604 has at least first and second retaining members, e.g., retaining members 622a, 622b, and can additionally include one or more retaining members, as illustrated by retaining member 622c. The retaining members are configured to couple the adjunct material 624 to the anvil 604. In the example illustrated, the retaining members can engage with openings formed in the adjunct material 624, such as openings 626a-626d, as discussed below.

As shown in FIG. 11, the retaining members 622a, 622c are disposed one side of the tissue-facing surface 618 in proximity to one edge 609a of the tissue-facing surface 618, and retaining member 622b is disposed at another, opposed side of the tissue-facing surface 618 in proximity to another, opposed edge 609b thereof. It should be appreciated that the tissue-facing surface 618 can have a fourth retaining member opposed to the retaining member 622c, which is not shown because of the partial view of the jaw 604 in FIG. 11. The retaining members 622a, 622b are disposed at opposed sides of the knife channel 608.

The retaining members can have a variety of different configurations. In the example illustrated, they are in the form of curved posts, or hooks, that extend from the tissue-facing surface 618 outward toward respective the edges 609a, 609b. For example, the retaining member 622a is curved towards the edge 609a, and the retaining member 622b is curved towards the edge 609b. However, the retaining members can have other shapes, as the described implementations are not limited in this respect. For example, the retaining members can be at least partially straight, have an hour glass shape, have a bulbous or widened end region, have one or more notches, be angled toward the edges of the tissue-facing surface, have roughness features, etc. The retaining members can be configured in any suitable manner suitable for assisting in retaining the adjunct on the jaw. Also, although three retaining members 622a, 622b and 622c are shown in FIG. 11, the tissue-facing surface 618 can have any other number of retaining members (e.g., one, two, or greater than three) configured to couple an adjunct thereto. Furthermore, the retaining members can be formed at various locations on the tissue-facing surface 618 of the anvil 604. For example, in some embodiments, two or more retaining members can be formed along each edge 609a, 609b of the tissue-facing surface 618. The retaining members can be formed at any suitable distance from one another that allows securely retaining the adjunct material on the jaw's tissue-facing surface. In addition, the retaining members can be disposed symmetrically with respect to the knife channel 608 or other features of the tissue-facing surface 618, or they can be formed at various other ways on the surface 618.

The retaining members 622a, 622b, 622c (and any retaining members which are not shown in FIG. 11) are configured to mate with respective mating features of the adjunct material 624. In particular, as mentioned above, the adjunct material 624 includes through openings 626a, 626b, 626c configured to receive the retaining members 622a, 622b, 622c, respectively. The fourth opening 626d is configured to engage a fourth retaining member, which is not shown in FIG. 11. The through openings 626a-626d in the adjunct 624 are sized to receive therein the respective retaining members. In this example, the openings are generally round, though it should be appreciated that the openings can have any other suitable shapes.

In the embodiment shown in FIG. 11, the adjunct material 624 is at least partially stretchable. For example, the adjunct 624 is formed such that substantially its entire area is at least partially stretchable. The adjunct 624 can be formed from any suitable material, for example, one or more suitable absorbable polymers. In embodiments in which the adjunct material is made from non-brittle polymers, deformations of the adjunct can be achieved through geometric changes (e.g., by reducing the adjunct's thickness until it becomes stretchy under a load, etc.). Additionally or alternatively, the adjunct material can be made at least partially stretchable by having one or more various features—for example, the adjunct can be in the form of a knitted sheet that has elasticity due to its geometry. The adjunct can be implemented as described, for example, in U.S. patent application Ser. No. 14/926,194, entitled "Extensible Buttress Assembly for Surgical Stapler," and filed on Oct. 29, 2015, which is hereby incorporated by reference herein in its entirety.

In some embodiments, as in the example illustrated, the adjunct material 624 includes at least one second, substantially non-stretchable portion. The one or more substantially non-stretchable portions can have a variety of configurations (including different configurations among the portions) and they can be disposed in any suitable manner in relation to substantially stretchable portions of the adjunct. FIG. 11 illustrates that the adjunct material 624 includes first and second non-stretchable portions 628a, 628b which can be associated with areas of the adjunct material 624 that are disposed over the staple-forming cavities 616 when the adjunct 624 is placed over the jaw 602. Thus, one or more areas of the adjunct 624 configured to be penetrated by the staples can be reinforced by being made substantially non-stretchable. In the illustrated implementation, the portions 628a, 628b are coupled to the adjunct material 624 such that the portions 628a, 628b are configured to be disposed between the tissue-facing surface 618 and the adjunct 624, and thus seat over the tissue-facing surface 618.

In some embodiments, it can be beneficial to attach the non-stretchable portions 628a, 628b to the adjunct 624 such that portions of the adjunct 624 disposed over the staple-forming cavities 616 are prevented from being stretched. In particular, if portions of the adjunct 624 that are disposed over staple-cavities 616 are stretched, then, when the adjunct 624 is stapled to tissue and released from the jaw 602, the adjunct 624 can damage tissue by pulling on the staples as it releases tension in areas where staples are formed. In this way, the non-stretchable portions can stabilize the staples and help protecting tissue being stapled.

Figure 12:
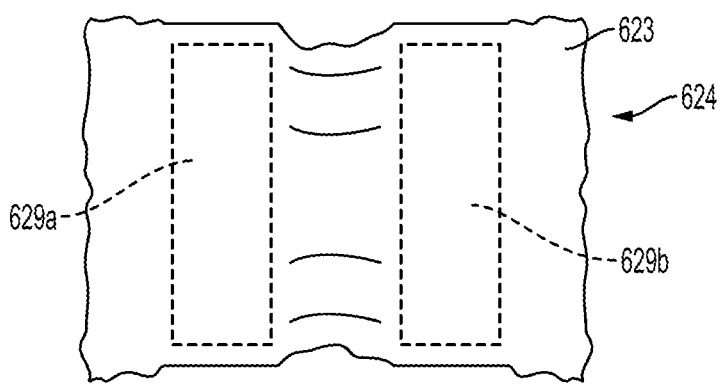
FIG. 12 is a schematic view of the adjunct material of FIG. 11, illustrating areas of the adjunct material configured to have non-stretchable portions.

The non-stretchable portions 628a, 628b can be formed in any suitable manner. For example, the portions 628a, 628b can be separate portions coupled to the adjunct 624. In at least one embodiment, the portions 628a, 628b are formed from PDO and coupled to (e.g., laminated onto), the stretchable adjunct 624. As an example, the portions 628a, 628b can be in the form of sheet laminates that are heat-pressed or otherwise attached onto the adjunct 624 to create the portions that are resistant to stretching. However, the portions 628a, 628b can be coupled to the adjunct 624 in various other ways, as the described techniques are not limited in any specific way in which one or more portions of at least partially stretchable adjunct are made substantially non-stretchable. FIG. 12 shows by way of example the adjunct 624 having a first, at least partially stretchable portion 623. As also schematically shown in FIG. 12, first and second areas 629a, 629b of the portion 623 of the adjunct 624 (which is, in this example, the entire adjunct) are configured to have portions 628a, 628b in the form of sheet laminates coupled thereto.

It should be appreciated that the two separate non-stretchable portions 628a, 628b are shown in FIG. 11 by way of example only. In some embodiments, one or more than two substantially non-stretchable portions can be associated with the adjunct material, and such portions can be disposed in various ways with respect to the stretchable portion(s) of the adjunct.

Furthermore, in at least one embodiment, the second portion can be in the form of a substantially non-stretchable second adjunct material that is coupled to the adjunct material and has any suitable size (e.g., it can have a smaller area than the "first" stretchable adjunct material). The second adjunct material is configured to reinforce and/or treat a treatment site in a patient, whereas the first stretchable adjunct material is configured to engage the first and second adjunct materials with the retaining members formed on the jaw. In some embodiments, the second adjunct can include drugs or other treating agents intended to be delivered to the treatment site. The non-stretchable portion(s) in the form of the second adjunct material can be coupled to the first adjunct material such that the second adjunct material is disposed on the tissue-facing surface of the jaw, similar to the non-stretchable portions 628a, 628b in FIG. 11. However, in some implementations, the second adjunct material can be disposed over the first adjunct material such that the stretchable adjunct material is disposed directly on the jaw.

It should further be appreciated that at least one substantially non-stretchable portion of the adjunct can be formed in other various ways. For example, the non-stretchable portion(s) can be part of the adjunct material. In particular, it can be in the form of at least one second portion having at least one property that is different from at least one property of other portions of the adjunct material. As an example, one or more portions of the adjunct (e.g., portions to be disposed over staple-forming or staple-holding cavities) can be more tightly woven, knitted, braded, or otherwise made non-stretchable or less stretchable than the remainder of the adjunct.

In use, the adjunct material 624 is configured to be releasably coupled with the anvil 604 by reversibly stretching at least a first portion of the adjunct (e.g., the at least partially stretchable portion) using an application of force such that, when the force is removed, the first portion transitions from a stretched configuration to a contracted configuration, thereby causing the adjunct material to be engaged with the retaining members. The adjunct material 624 couples with the anvil 604 in a secure manner, which helps ensure that the adjunct 624 remains coupled to the anvil 604 while the end effector 100 is manipulated as desired using a surgical procedure. The adjunct is held in engagement with the anvil 604 until an action, such as an activation of the end effector 600 to release staples from its cartridge and/or an activation of a cutting element, is taken that causes the separation of the adjunct 624 from the anvil 604.

Figure 13A:
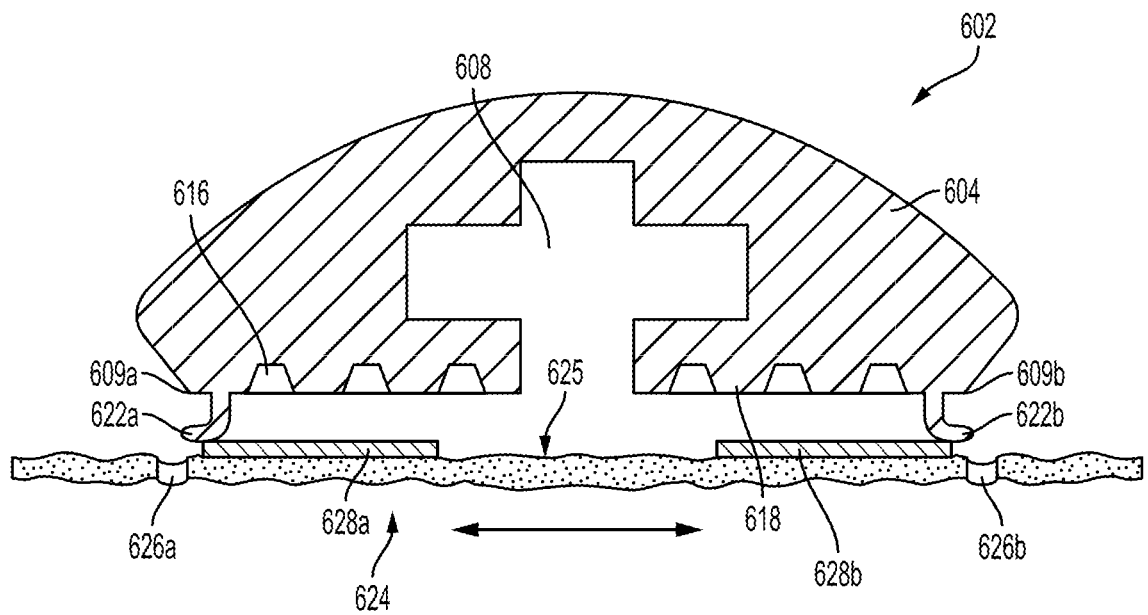
FIG. 13A is a cross-sectional view of a jaw of an end effector and at least partially stretchable adjunct material to be releasably coupled to the jaw.
Figure 13B:
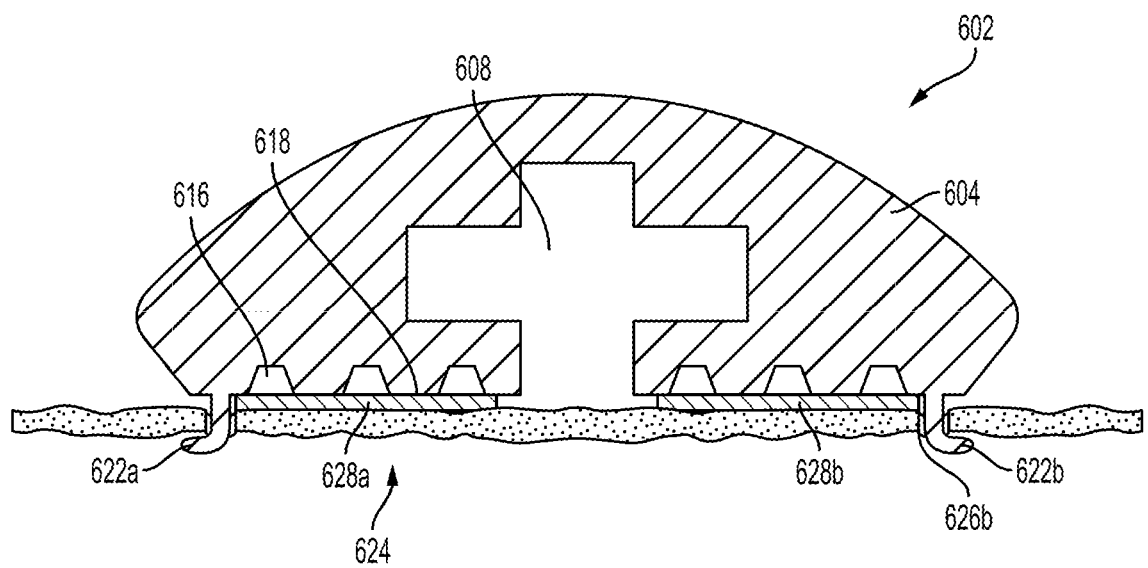
FIG. 13B is a cross-sectional view of the jaw of FIG. 13A, illustrating the adjunct material releasably coupled to the jaw.

FIGS. 13A and 13B illustrate an example of a method of coupling the adjunct material 624 with the jaw 602. FIG. 13A shows the jaw 602 and the adjunct 624 prior to the adjunct 624 being coupled to the jaw 602. As shown schematically in FIG. 13A, the adjunct 624 is being stretched such that the openings 626a, 626b in the adjunct 624 extend beyond the retaining members 622a, 622b formed on the jaw 602.

The adjunct material 624 has at least one portion configured to be reversibly stretched using application of a force. FIG. 13A shows a cross-section view of the upper jaw 602 wherein the adjunct 624 is stretched prior to being coupled to the upper jaw 602, adjacent the tissue-facing surface 618. As illustrated by the double-ended arrow, the adjunct 624 is stretched laterally across the tissue-facing surface 608 of the upper jaw 602. In this example, non-stretchable portions 628a, 628b are attached to the adjunct 624 between the adjunct 624 and the tissue-facing surface 618 of the upper jaw 602 such that the areas of the adjunct 624 having the portions 628a, 628b coupled thereto substantially do not stretch. In FIG. 13A, the portions of the adjunct 624 that do not have the portions 628a, 628b coupled thereto, e.g., portion 625 and other remaining adjunct's portions, are shown stretched such that the openings 626a, 626b extend beyond the retaining members 622a, 622b.

The at least one portion of the adjunct material 624, such as the portion 625, can be stretched using application of a force, as discussed in more detail below. When the force is removed, the stretched portion transitions from a stretched configuration to a contracted configuration, which causes the adjunct material 624 to be engaged with the first and second retaining members 622a, 622b. Thus, FIG. 13B shows the upper jaw 602 with the adjunct coupled to the tissue-facing surface 618 thereof via the retaining members 622a, 622b. In particular, the retaining members 622a, 622b are received in openings 626a, 626b such that the adjunct is retained on the jaw. The adjunct material 624 is thus held in tension by the retaining members 626a, 626b engaged with the openings 626a, 626b such that a possibility of the adjunct material 624 prematurely slipping off the jaw is decreased or eliminated. During a surgical procedure, after the jaw 602 with the adjunct material 624 coupled thereto is manipulated and positioned as desired, the firing of staples and/or a cutting element releases the tension such that the adjunct material 624 slips off the retaining members 626a, 626b and becomes separated from the jaw 602.

Figure 14A:
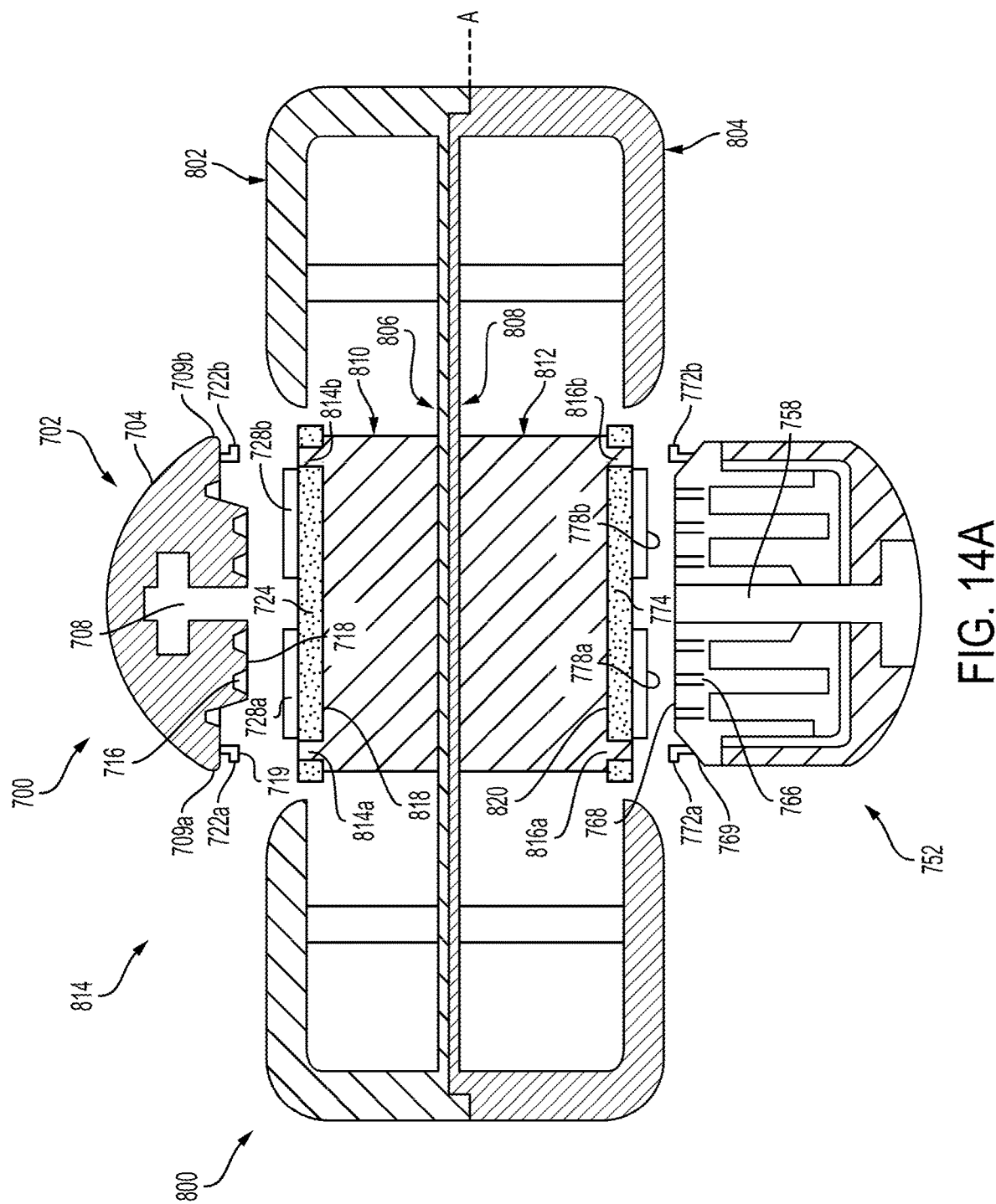
FIG. 14A is a cross-sectional view of jaws of an end effector and a loader prior to adjuncts being releasably coupled to the jaws.
Figure 14B:
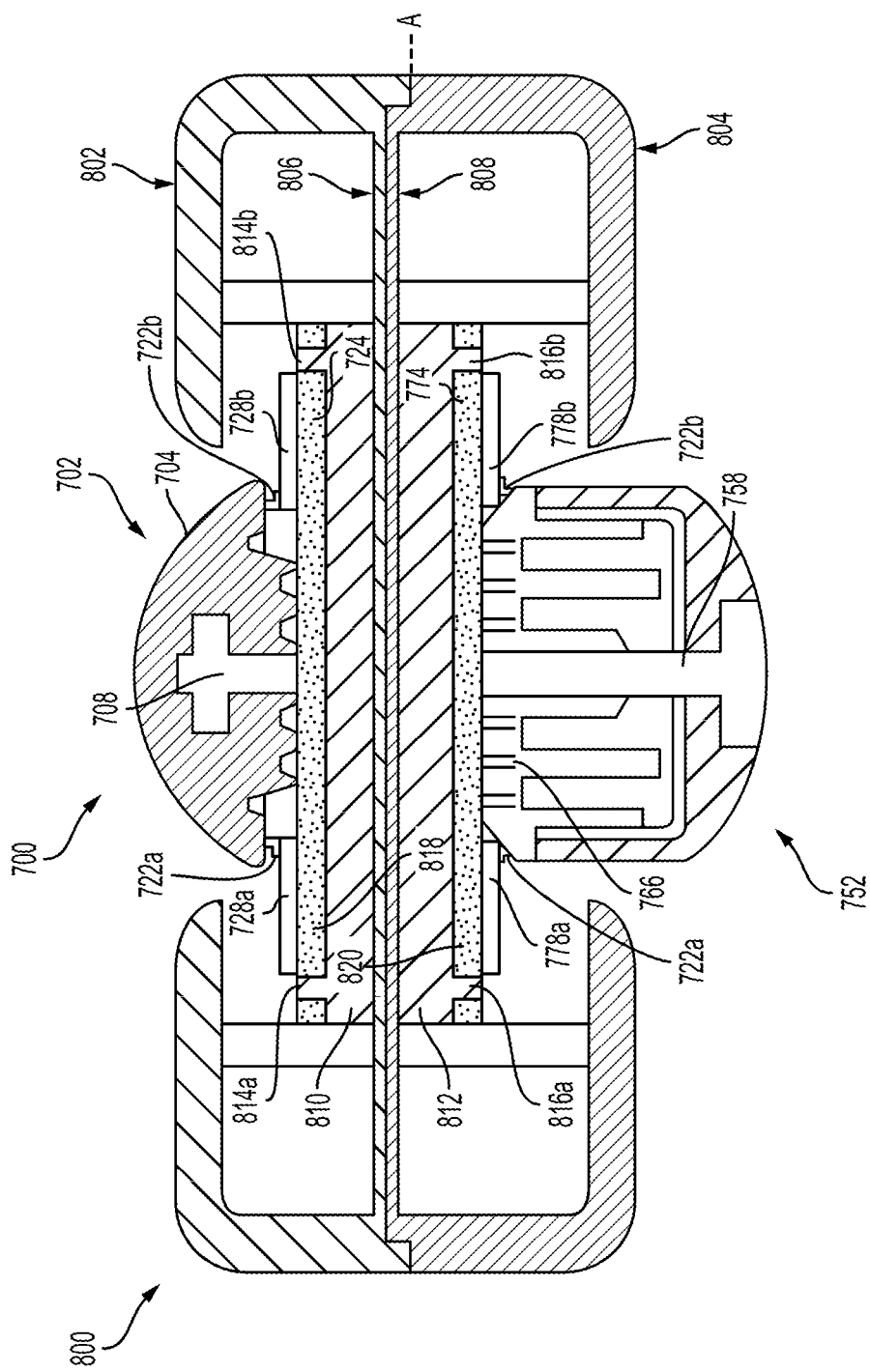
FIG. 14B is a cross-sectional view of the jaws and the loader of FIG. 14A, illustrating the jaws and the loader while the adjuncts are being transferred from the loader to the jaws.
Figure 14C:
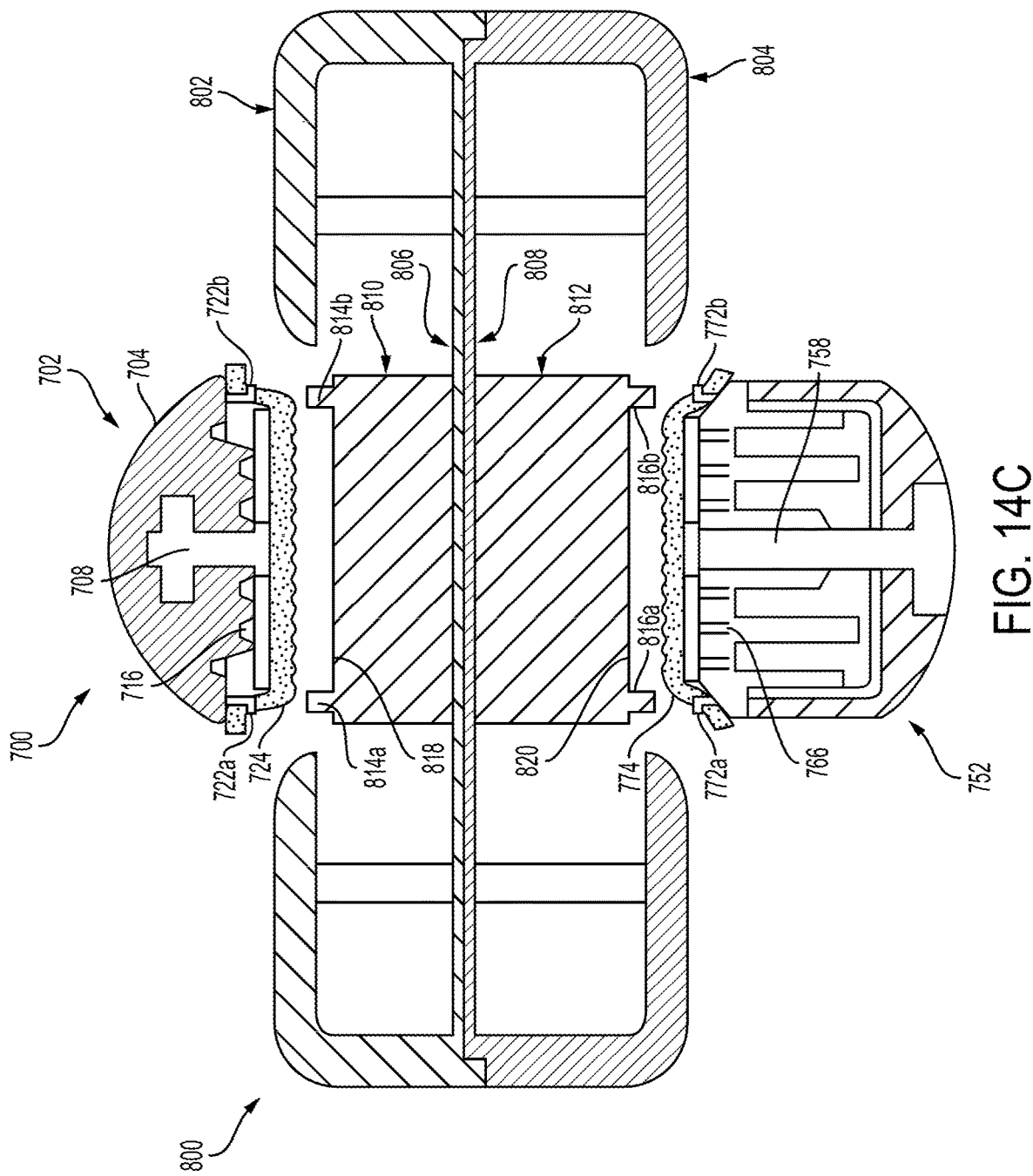
FIG. 14C is a cross-sectional view of the jaws and the loader of FIG. 14A, illustrating the jaws and the loader after the adjuncts have been transferred from the loader to the jaws and are releasably coupled to the jaws.

At least partially stretchable adjunct can be attached to one or both jaws of an end effector in a number of various ways. For example, in some embodiments, one or more adjuncts can be attached to jaws of an end effector using a removable loader member configured to releasably retain an adjunct material thereon until the adjunct material is applied to at least one jaw. FIGS. 14A-14C illustrate an example of an end effector 700 that can be used with a member or loader 700, to attach one or more adjunct materials or adjuncts to the end effector 800.

The end effector 700 can generally include components similar to those described with regard to end effector 600, and can also include features and/or components that facilitate attaching one or more adjuncts thereto using a loader, e.g., loader 800, to attach adjuncts . Thus, the end effector 700 includes a first (upper in FIGS. 14A-14C) jaw 702 having an anvil 704 and a second (lower in FIGS. 14A-14C) jaw 752 having a cartridge body. In this example, the loader 800 is configured to apply first and second adjuncts 724, 774 to the first and second jaws 702, 752, respectively.

FIG. 14A shows a cross-sectional view of the end effector 700, wherein the jaws 702, 752 of the end effector 700 are disposed over the loader 800 prior to the adjuncts 724, 774 being coupled to the jaws 702, 752. As shown in FIG. 14A, in this example, the anvil 704 includes a multi-level (e.g., a two-plane or two-level) tissue-facing surface formed of surfaces 718, 719, wherein the surface 718 extends in a plane closer to the cartridge 752 and the surfaces 719 are stepped out surfaces disposed in a plane that is further away from the cartridge 752. At least portions of the tissue-facing surfaces 718, 719, have staple-forming cavities 716 formed thereon. However, in some embodiments, the stepped surfaces 719 may not have staple-forming cavities. The tissue-facing surface 718 has a knife channel 708 configured to receive a cutting element (e.g., a knife). It should be appreciated that the anvil 704 is shown to have the two-level tissue-facing surface by way of example only, as the anvil 704 can have a tissue-facing surface formed in substantially one planes, or, in some implementations, in more than two planes.

As shown in FIG. 14A, the tissue-facing surfaces 719 of the anvil 704 have at least first and second retaining members 722a, 722b formed thereon. The tissue-facing surfaces 719 can additionally include other retaining members, similar to those discussed above with regard to end effector 600. For example, each of distal and proximal ends of the tissue-facing surfaces 719 can have two retaining members. However, other number and positions of the retaining members can be implemented additionally or alternatively. The retaining members are configured to couple the adjunct material 724 to the anvil 704. In the example illustrated, the retaining members can engage with openings formed in the adjunct material, as discussed below.

The cartridge 752 has a plurality of staple-holding cavities 766 configured to seat staples therein, the staple-holding cavities 766 opening on tissue-facing surface 768 of the cartridge 752. The staple cavities can form a certain pattern on the tissue-facing surfaces 768, which corresponds to a pattern of the staple-forming cavities 716 formed in the anvil 704. The cartridge includes first and second retaining members 772a, 772b, located on angled surfaces 769 that are adjacent to the tissue-facing surface 768. The retaining members 772a, 772b disposed on the angled surfaces 769 are configured to releasably couple the adjunct material 774 to the cartridge jaw 752. As also shown, the tissue-facing surface 768 has a knife channel 758 configured to receive a cutting element (e.g., a knife). It should be appreciated that the cartridge 752 is shown to have the angled surfaces 769 by way of example only, as the cartridge 752 may not have such surfaces in other implementations, or it may have other suitable configurations.

The loader 800 can have any suitable configuration. In the example illustrated, the loader 800 can be in the form of a generally rectangular frame-like holder configured to releasably couple one or more adjuncts to one or both jaws of the end effector. As shown in FIGS. 14A-14C, the loader 800 can be in the form of a first (e.g., top) and second (e.g., bottom) generally rectangular housings 802 and 804 coupled to one another along interface A. Jaw-facing surfaces 806, 808, of the loader 800 can have compressible (e.g., elastic, or pliable), members or bodies 810, 812, attached thereon. The compressible bodies 810, 812 can be made of, e.g., silicone, or any other compressible and at least partially resilient material suitable for being compressed. The elastic members 810, 812 can include gripping members 814a, 814b, 816a, 816b, that extend from jaw-facing surfaces 818, 820, respectively.

As illustrated in FIG. 14A, the adjuncts 724, 774, can be coupled to the elastic members 810, 812 of the loader 800, which can be done during assembly of the loader 800, or at any other time. The adjuncts 724, 774 can be substantially similar to adjunct 624 (FIGS. 13A and 13B), and they can include openings, which can be mated with gripping members 814a, 814b, and 816a, 816b, to releasably secure the adjuncts to the elastic members 810, 812. Similar to the adjunct 624, adjuncts 724, 774 each include first and second non-stretchable portions 728a, 728b, 778a, 778b.

To apply the adjuncts 724, 774 to the jaws 702, 752, the jaws 702, 752 can be clamped over the loader 800 having the elastic members 810, 812 coupled to the adjuncts 724, 774, as illustrated in FIG. 14B. The clamping action causes the jaws 702, 752 to apply a force to the elastic members 810, 812 which, as a result, compress and stretch laterally, thereby causing the adjunct to also stretch, as shown in FIG. 14B. As also shown, the elastic members 810, 812 are configured to move from their original, non-compressed configuration to a compressed configuration such that they stretch in a substantially uniform manner, such that one or more portions of the adjuncts 724, 774 can also be stretched in a substantially evenly manner. In the illustrated example, the tissue-facing surfaces 718, 768 are configured to engage the adjunct prior to the retaining members 722a, 722b, 772a, 772b, which can allow the adjunct to expand without getting caught on the retaining members 722a, 722b, 772a, 772b.

When the jaws 702, 752 are opened and the clamping force applied by the jaws 702, 752 is removed, as shown in FIG. 14C, the adjuncts 724, 774 are released from the engagement with the elastic members 810, 812, which at least partially return to their original, non-compressed configuration, as also shown. This causes the adjuncts 724, 774 to at least partially contract. When sufficient contraction has occurred, the adjuncts 724, 774 are separated from the loader 800. For example, the openings in the adjuncts 724, 774 can mate with the retaining members 722a, 722b, 772a, 772b that thus displace the gripping members 814a, 814b, 816a, 816b previously engaged with the openings. Additionally or alternatively, in some embodiments, the retaining members 722a, 722b, 772a, 772b formed on the jaws 702, 752 can engage portions of the adjuncts 724, 774 other than the openings. For example, one or more portions of the adjuncts can be stretched (as shown in FIG. 14B), then at least partially contracted and engaged with the retaining members 722a, 722b, 772a, 772b.

Regardless of the specific way in which the retaining members 722a, 722b, 772a, 772b can mate with the adjuncts 724, 774, the adjuncts 724, 754 are released from the gripping members 814a, 814b and become coupled to the jaws 702, 752, as illustrated in FIG. 14C. The adjuncts 724, 754 can be held over the jaws 702, 752 in at least partially stretched configuration. In this example, the substantially non-stretchable portions 728a, 728b, 778a, 778b of the adjuncts 724, 754 can be disposed over the jaws so as to be penetrated by the staples when the staples are ejected. The loader 800 can then be removed. In use, after the end effector 700 is manipulated as desired during a surgical procedure, the firing of the staples and/or a cutting element causes the adjuncts 724, 754 to separate from the jaws.

It should be appreciated that, although in FIGS. 14A-14C the loader 800 is configured to deliver the adjuncts 724, 774 to both of the jaws 702, 752, in some embodiments the loader 800 can be used to apply one of the adjuncts to one of the jaws. It should also be appreciated that the loader 800 is shown by way of example only, as at least partially stretchable adjunct can be applied to one or both jaws of an end effector using a loader having any other suitable configuration.

In the embodiments described above, an adjunct material can be releasably coupled to a jaw of an end effector during manufacturing of the end effector or during a surgical procedure. Furthermore, the embodiments can have different variations. For example, a jaw of an end effector having a cartridge can seat a removable and replaceable cartridge, or the entire jaw with a cartridge can be removable and replaceable. A jaw can also be part of a disposable loading unit configured to be coupled distally to a shaft of a surgical instrument. As another example, although the systems and methods for releasably retaining an adjunct material over a jaw of an end effector are described in connection with linear staplers of various configurations, it should be appreciated that the described techniques can be implemented in connection with circular surgical staplers, e.g., circular surgical stapler 80 as illustrated in FIG. 5.

A person skilled in the art will appreciate that the described subject matter has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. An end effector for a surgical instrument, comprising:
a first jaw having a cartridge with a plurality of staple cavities configured to seat staples therein, the staple cavities opening on a tissue-facing surface of the cartridge;
a second jaw opposing the first jaw and having an anvil with a plurality of staple forming cavities formed on a tissue-facing surface thereof, wherein the first and second jaws are configured to clamp tissue therebetween;
first and second retaining members disposed on a tissue-facing surface of at least one jaw of the first and second jaws;
an adjunct material configured to be releasably retained on the at least one jaw; and
a contractible attachment feature configured to transition from an original, non-contracted configuration to a contracted configuration under application of heat, wherein in the non-contracted configuration, the contractible attachment feature engages with the first and second retaining members under a first tension, and wherein in the contacted configuration, the contractible attachment feature engages with the first and second retaining members under a second tension that is greater than the first tension to thereby couple the adjunct material with the first and second retaining members.

2. The end effector of claim 1, wherein the first retaining member is disposed at one side of a tissue-facing surface of the at least one jaw in proximity to one edge of the tissue-facing surface of the at least one jaw, and the second retaining member is disposed at another, opposed side of the tissue-facing surface in proximity to another, opposed edge of the tissue-facing surface.

3. An end effector for a surgical instrument, comprising:
a first jaw having a cartridge with a plurality of staple cavities configured to seat staples therein, the staple cavities opening on a tissue-facing surface of the cartridge;
a second jaw opposing the first jaw and having an anvil with a plurality of staple forming cavities formed on a tissue-facing surface thereof, wherein the first and second jaws are configured to clams tissue therebetween;
at least one first and second retaining members disposed on a tissue-facing surface of at least one jaw of the first and second jaws;
an adjunct material configured to be releasably retained on the at least one jaw; and
a contractible attachment feature configured to be transitioned from an original, non-contracted configuration to a contracted configuration under application of heat, wherein the attachment feature is engaged with the adjunct material, and contraction of the attachment feature is effective to couple the adjunct material with the first and second retaining members, and wherein the attachment feature is disposed over at least a portion of the adjunct material and comprises a strand of a shrinkable polymer that is arranged in at least one loop encompassing both the first and second retaining members, the shrinkable polymer being contracted such that the at least one loop is engaged around the first and second retaining members and thereby releasably retains the adjunct material over the at least one jaw.

4. The end effector of claim 3, wherein the strand of the shrinkable polymer passes through at least one portion of the adjunct material.

5. The end effector of claim 3, wherein the attachment feature comprises a plurality of polymer strands interwoven into the adjunct material such that at least one first strand is disposed along a longitudinal axis of the adjunct material and at least one second strand is disposed along an axis substantially perpendicular to the longitudinal axis.

6. The end effector of claim 5, wherein the adjunct material comprises a plurality of through openings, the openings comprising at least first and second openings configured to be mated with the first and second retaining members when the plurality of polymer strands are in the contracted configuration and thereby cause the at least the first and second openings in the adjunct material to constrict around the first and second retaining members.

7. The end effector of claim 6, wherein the polymer strands are interwoven into the adjunct material by being passed through at least some of the plurality of through openings.

8. A method of assembling an end effector for a surgical instrument, the end effector having a first jaw having a cartridge with a plurality of staple cavities configured to seat staples therein and opening on a tissue-facing surface of the cartridge, and a second jaw opposing the first jaw and having an anvil with a plurality of staple forming cavities formed on a tissue-facing surface thereof, the method comprising:
  associating an adjunct material with at least one contractible attachment feature configured to be transitioned from an original, non-contracted configuration to a contracted configuration under application of heat; and
  applying heat to the adjunct material to cause the at least one contractible attachment feature to contract and thereby cause the adjunct material to be releasably retained on the at least one jaw by coupling the adjunct material with first and second retaining members disposed on a tissue facing surface of at least one jaw of the first and second jaws,
  wherein applying the heat to the adjunct material further comprises coupling the at least one contractible attachment feature with first and second retaining members.

9. An end effector for a surgical instrument, comprising:
  a first jaw having a cartridge with a plurality of staple cavities configured to seat staples therein, the staple cavities opening on a tissue-facing surface of the cartridge;
  a second jaw opposing the first jaw and having an anvil with a plurality of staple forming cavities formed on a tissue-facing surface thereof, wherein the first and second jaws are configured to clamp tissue therebetween;
  first and second retaining members disposed on a tissue-facing surface of at least one jaw of the first and second jaws;
  an adjunct material configured to be releasably retained on the at least one jaw; and
  a contractible attachment feature engaged with the adjunct material and configured to transition from an original, non-contracted configuration to a contracted configuration under application of heat, wherein contraction of the contractible attachment feature is effective to couple the contractible attachment feature and the adjunct material with the first and second retaining members.

10. The end effector of claim 9, wherein the first retaining member is disposed at one side of a tissue-facing surface of the at least one jaw in proximity to one edge of the tissue-facing surface of the at least one jaw, and the second retaining member is disposed at another, opposed side of the tissue-facing surface in proximity to another, opposed edge of the tissue-facing surface.

* * * * *